US008963025B2

(12) United States Patent  (10) Patent No.: US 8,963,025 B2
Pollock et al.  (45) Date of Patent: *Feb. 24, 2015

(54) SURGICAL OBJECT AND FLUID MONITORING SYSTEM HAVING HIGHLY SENSITIVE AND RELIABLE DETECTION OF OBJECTS BEING PLACED IN A CONTAINER

(71) Applicant: Surgitrac Corporation, Boca Raton, FL (US)

(72) Inventors: Richard A. Pollock, Atlanta, GA (US); Mahmood S. Kassam, Ontario (CA)

(73) Assignee: Surgitrac Corporation, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,166

(22) Filed: Apr. 7, 2014

(65) Prior Publication Data

US 2014/0262553 A1  Sep. 18, 2014

Related U.S. Application Data

(63) Continuation-in-part of application No. 13/839,042, filed on Mar. 15, 2013, now Pat. No. 8,692,140, and a continuation-in-part of application No. 13/839,450, filed on Mar. 15, 2013, now Pat. No. 8,704,178.

(51) Int. Cl.
*A61B 19/00*  (2006.01)
*G01G 19/40*  (2006.01)
(Continued)

(52) U.S. Cl.
CPC .............. *G01G 19/387* (2013.01); *A61B 19/00* (2013.01); *G01G 19/40* (2013.01); *G01G 19/414* (2013.01); *G01G 19/42* (2013.01)
USPC ....... 177/15; 177/25.13; 177/25.19; 177/238; 604/403; 604/404; 604/317; 604/318

(58) Field of Classification Search
CPC ..... G01G 17/04; G01G 19/414; G01G 21/23; G01G 21/28; A61B 5/02042; A61B 2019/4826; A61B 2019/448; G06F 19/327

USPC ............. 177/15, 25.13, 25.19, 126, 238, 244; 604/317, 318, 403, 404

See application file for complete search history.

(56) References Cited

U.S. PATENT DOCUMENTS 3,367,431 A  2/1968  Baker
3,613,899 A  10/1971  Schleicher et al.
(Continued)

FOREIGN PATENT DOCUMENTS

WO  2004047660  6/2004
WO  2011075433  6/2011
(Continued)

OTHER PUBLICATIONS

O'Connor, Anahad, "When Surgeons Leave Objects Behind", New York Times, pp. 1-4, Sep. 24, 2012.
(Continued)

*Primary Examiner* — Randy W Gibson
(74) *Attorney, Agent, or Firm* — Fleit Gibbons Gutman Bongini & Bianco PL; Jose Gutman

(57) ABSTRACT

A surgical sponge and fluid monitoring system and method are provided. The system (100) includes a support ring (104) for securely supporting a container (101) with at least one port opening (206) for placing sponges (204) into the container through the at least one port opening. The support ring includes RFID communication circuitries (305, 307) that interrogate an RFID device (205) in the sponge (204) and an RFID device in the container. The support ring is mechanically linked to a load cell (706, 1329) in the system. The processor (1302) reliably detects when a sponge is placed into the container through the at least one port opening, identifies the type of sponge placed into the container, counts the number of sponges in the container, sorts the types of sponges, and calculates fluid loss for a patient in a surgical procedure. A user interface (1308, 114) keeps the medical professionals informed.

23 Claims, 11 Drawing Sheets

(51) Int. Cl.
   *G01G 19/414* (2006.01)
   *G01G 19/42* (2006.01)
   *G01G 19/387* (2006.01)

(56) References Cited

U.S. PATENT DOCUMENTS

| | | | |
|---|---|---|---|
| 3,808,694 A * | 5/1974 | Hutchinson et al. | 33/512 |
| 3,890,907 A * | 6/1975 | Peterson | 108/136 |
| 3,905,311 A * | 9/1975 | Carpentier | 108/136 |
| 3,986,697 A * | 10/1976 | Amor et al. | 248/333 |
| 4,041,320 A * | 8/1977 | Amor et al. | 378/194 |
| 4,057,891 A * | 11/1977 | Amor et al. | 29/434 |
| 4,295,537 A | 10/1981 | McAvinn et al. | |
| 4,361,231 A | 11/1982 | Patience | |
| 4,419,232 A * | 12/1983 | Arntyr et al. | 210/164 |
| 4,422,548 A | 12/1983 | Cheesman et al. | |
| 4,478,332 A | 10/1984 | Wiestmiller | |
| 4,903,837 A | 2/1990 | Duello | |
| 4,922,922 A | 5/1990 | Pollock et al. | |
| 5,009,275 A | 4/1991 | Sheehan | |
| 5,031,642 A | 7/1991 | Nosek | |
| 5,033,703 A * | 7/1991 | Allen, Sr. | 248/97 |
| 5,227,765 A | 7/1993 | Ishizuka et al. | |
| 5,258,742 A | 11/1993 | Soldevila Domingo et al. | |
| 5,285,682 A * | 2/1994 | Micklish | 73/149 |
| 5,425,069 A * | 6/1995 | Pellegrino et al. | |
| 5,443,082 A | 8/1995 | Mewburn | |
| 5,629,498 A * | 5/1997 | Pollock et al. | 177/15 |
| 5,641,947 A | 6/1997 | Riddle, Jr. | |
| 5,650,596 A | 7/1997 | Morris et al. | |
| 5,664,582 A | 9/1997 | Szymaitis | |
| 5,836,553 A * | 11/1998 | Bergaila | 248/99 |
| 5,889,530 A | 3/1999 | Findlay | |
| 5,918,197 A | 6/1999 | Toussant et al. | |
| 5,923,001 A | 7/1999 | Morris et al. | |
| 5,931,824 A | 8/1999 | Stewart et al. | |
| 6,026,818 A | 2/2000 | Blair et al. | |
| 6,302,461 B1 | 10/2001 | Debras et al. | |
| 6,777,623 B2 | 8/2004 | Ballard | |
| 6,777,625 B2 | 8/2004 | Oldendorf | |
| 6,781,067 B2 | 8/2004 | Montagnino et al. | |
| 6,900,396 B2 | 5/2005 | Murdter | |
| 6,998,541 B2 | 2/2006 | Morris et al. | |
| 7,001,366 B2 | 2/2006 | Ballard | |
| 7,019,650 B2 | 3/2006 | Volpi et al. | |
| 7,100,722 B2 * | 9/2006 | Bowen | 180/65.51 |
| 7,297,834 B1 | 11/2007 | Shapiro | |
| D557,421 S | 12/2007 | Fleck et al. | |
| 7,311,161 B2 * | 12/2007 | Lee | 180/19.1 |
| D568,186 S | 5/2008 | Blair et al. | |
| 7,378,604 B2 | 5/2008 | Truong | |
| 7,378,694 B2 | 5/2008 | Yi et al. | |
| 7,378,904 B2 | 5/2008 | Risbo | |
| 7,411,506 B2 | 8/2008 | Volpi et al. | |
| 7,469,727 B2 | 12/2008 | Marshall | |
| 7,501,948 B2 | 3/2009 | Roemerman et al. | |
| 7,512,583 B2 | 3/2009 | Benson et al. | |
| 7,526,455 B2 | 4/2009 | Benson et al. | |
| 7,541,933 B2 | 6/2009 | Volpi et al. | |
| 7,557,711 B2 | 7/2009 | Volpi et al. | |
| D603,048 S | 10/2009 | Fleck et al. | |
| 7,609,159 B2 | 10/2009 | Benson et al. | |
| 7,656,286 B2 | 2/2010 | Benson et al. | |
| D611,610 S | 3/2010 | Fleck et al. | |
| 7,671,744 B2 | 3/2010 | Volpi et al. | |
| 7,696,877 B2 | 4/2010 | Barnes et al. | |
| 7,703,674 B2 | 4/2010 | Stewart et al. | |
| 7,735,788 B2 * | 6/2010 | Newkirk et al. | 248/129 |
| 7,755,491 B2 | 7/2010 | Volpi et al. | |
| 7,760,097 B2 | 7/2010 | Volpi et al. | |
| 7,764,178 B2 | 7/2010 | Volpi et al. | |
| 7,784,468 B2 | 8/2010 | Fabian et al. | |
| D624,531 S | 9/2010 | Fleck et al. | |
| 7,795,491 B2 | 9/2010 | Stewart et al. | |
| 7,893,840 B2 | 2/2011 | Volpi et al. | |
| 7,898,420 B2 | 3/2011 | Blair et al. | |
| 8,056,162 B2 * | 11/2011 | Newkirk et al. | 5/510 |
| 8,063,760 B2 | 11/2011 | Volpi et al. | |
| 8,105,296 B2 | 1/2012 | Morris et al. | |
| 8,111,162 B2 | 2/2012 | Barnes et al. | |
| 8,174,366 B2 | 5/2012 | Volpi et al. | |
| 8,181,860 B2 | 5/2012 | Fleck et al. | |
| 8,256,674 B2 | 9/2012 | Fleck et al. | |
| 8,692,140 B1 * | 4/2014 | Pollock et al. | 177/15 |
| 8,704,178 B1 * | 4/2014 | Pollock et al. | 250/336.1 |
| 2002/0050112 A1 * | 5/2002 | Koch et al. | 52/651.07 |
| 2003/0062221 A1 * | 4/2003 | Burrow et al. | |
| 2006/0151059 A1 * | 7/2006 | Ours et al. | 141/314 |
| 2006/0278447 A1 * | 12/2006 | Lee | 180/15 |
| 2007/0252919 A1 * | 11/2007 | McGreevy | 348/825 |
| 2007/0285249 A1 | 12/2007 | Blair et al. | |
| 2008/0204245 A1 | 8/2008 | Blair et al. | |
| 2010/0033309 A1 | 2/2010 | Blair | |
| 2010/0108079 A1 | 5/2010 | Blair | |
| 2010/0109848 A1 | 5/2010 | Blair et al. | |
| 2010/0283314 A1 * | 11/2010 | Lubbers et al. | 303/9.61 |
| 2011/0004276 A1 | 1/2011 | Blair et al. | |
| 2011/0163854 A1 * | 7/2011 | Hamelin et al. | 340/10.1 |
| 2011/0181394 A1 | 7/2011 | Blair | |
| 2011/0229252 A1 * | 9/2011 | Roither et al. | 403/109.2 |
| 2012/0298459 A1 * | 11/2012 | Lubbers et al. | 188/159 |

FOREIGN PATENT DOCUMENTS

| | | |
|---|---|---|
| WO | 2011156671 | 12/2011 |
| WO | 2012078500 | 6/2012 |

OTHER PUBLICATIONS

European Examination report dated Jul. 9, 2014 received for European Application No. 14159722.9.
European Search Report dated Sep. 26, 2014 received for Application No. 14159723.7.

* cited by examiner

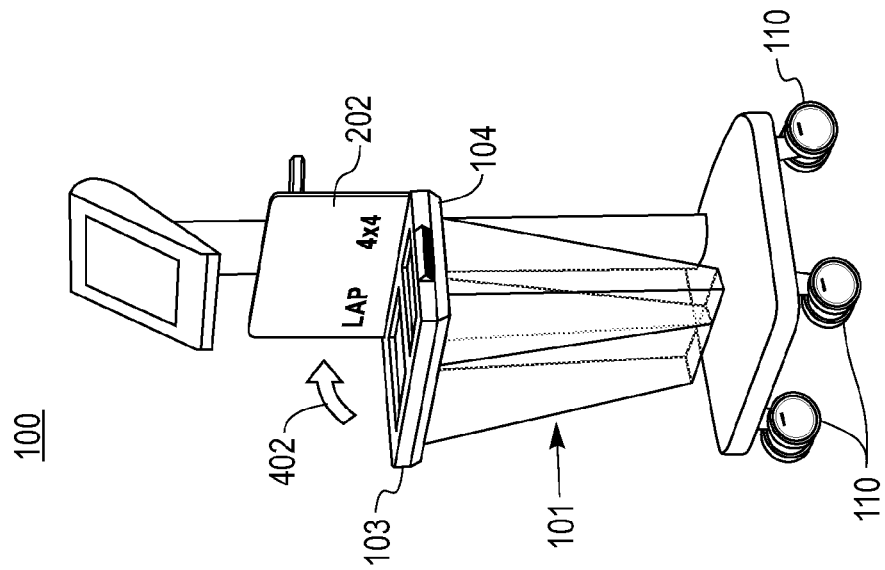
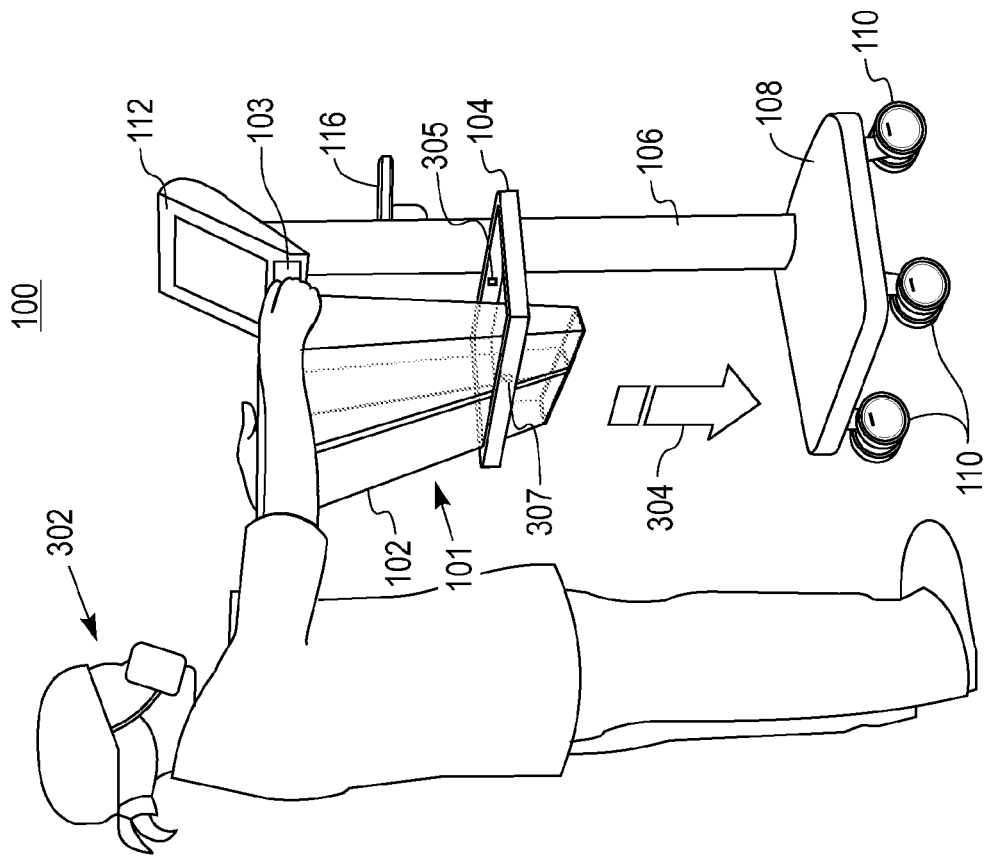

SURGICAL OBJECT AND FLUID MONITORING SYSTEM HAVING HIGHLY SENSITIVE AND RELIABLE DETECTION OF OBJECTS BEING PLACED IN A CONTAINER

CROSS-REFERENCE TO RELATED APPLICATIONS

This application is based upon and claims priority to U.S. patent application Ser. No. 13/839,042, entitled "SURGICAL OBJECT AND FLUID MONITORING SYSTEM HAVING HIGHLY SENSITIVE AND RELIABLE DETECTION OF OBJECTS BEING PLACED IN A CONTAINER", filed on Mar. 15, 2013, the disclosure of which is hereby incorporated by reference in its entirety. This application is based upon and claims priority to U.S. patent application Ser. No. 13/839,450, entitled "CONTAINER FOR SURGICAL OBJECT AND FLUID MONITORING SYSTEM", filed on Mar. 15, 2013, the disclosure of which is hereby incorporated by reference in its entirety.

FIELD OF THE DISCLOSURE

The present disclosure generally relates to surgical object monitoring systems, and more particularly to a surgical object (e.g., a surgical sponge) monitoring system that can monitor and track surgical objects and the fluid of a patient during a surgical procedure.

BACKGROUND

Surgical object monitoring systems have attempted to keep track of surgical objects with varying degrees of success. Some monitoring systems have relied almost entirely on manual counting of objects, such as sponges, while being used in a surgical operating room. This manual tracking process can be particularly error prone, which can result in unfortunate cases of surgical objects remaining inside patients after a surgical operation. Some monitoring systems have attempted to utilize complex and expensive technical solutions utilizing objects modified with RFID devices and/or barcodes to be scanned before, during, and after surgical procedures. These conventional monitoring systems continue to experience problems in attempting to keep track, and possibly locate lost objects such as sponges, that remain inside a patient. These conventional monitoring systems also fail to monitor fluids, such as blood, serum, or other fluids, that can be lost by a patient during a surgical procedure.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIGS. 1 to 5 are perspective views of an example of a monitoring system for use during a surgical procedure, according to the present disclosure;

DETAILED DESCRIPTION

Figure 2:
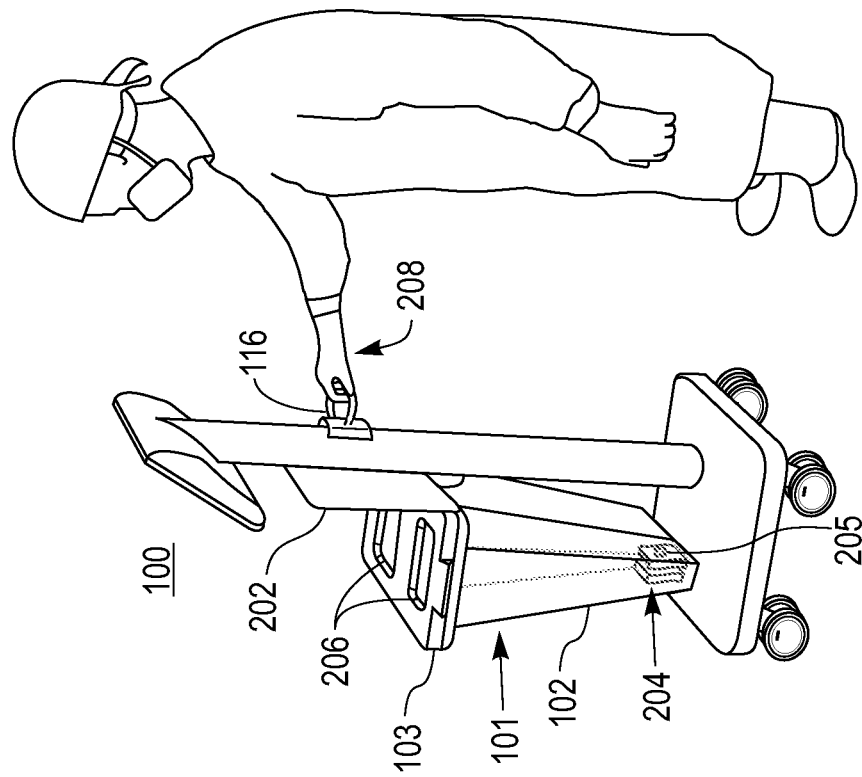

As required, detailed embodiments are disclosed herein; however, it is to be understood that the disclosed embodiments are merely examples and that the devices, systems and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, commanded, altered, modified, built, composed, constructed, designed, or that has any combination of these characteristics to carry out a given function. The term "adapted to" describes hardware, software or a combination of hardware and software that is capable of, able to accommodate, to make, or that is suitable to carry out a given function.

The terms "controller", "computer", "server", "client", "computer system", "computing system", "personal computing system", or "processing system" describe examples of a suitably configured processing system adapted to implement one or more embodiments of the present disclosure. Any suitably configured processing system is similarly able to be used by embodiments of the present disclosure. A processing system may include one or more processing systems or processors. A processing system can be realized in a centralized fashion in one processing system or in a distributed fashion where different elements are spread across several interconnected processing systems.

The terms "computing system", "computer system", and "personal computing system", describe a processing system that includes a user interface and which is suitably configured and adapted to implement one or more embodiments of the present disclosure. The terms "network", "computer network", "computing network", and "communication network", describe examples of a collection of computers and devices interconnected by communications channels that facilitate communications among users and allows users to share resources. The terms "wireless network", "wireless communication network", and "wireless communication system", similarly describe a network and system that communicatively couples computers and devices primarily or entirely by wireless communication media. The terms "wired network" and "wired communication network" similarly describe a network that communicatively couples computers and devices primarily or entirely by wired communication media.

The terms "in proximity", "in the near vicinity", and the like, when used herein with respect to short range communications with RFID devices are intended to broadly describe the typical distance suitable for effective short range communications with the RFID devices, according to various well known specifications and types of short range communications and standards. Such typical distance can, and will likely, evolve according to future specifications of short range communications and evolving short range communications standards. Therefore, these terms such as "in proximity", "in the near vicinity", and the like, should be considered only for understanding the current examples and not for any limitation of an embodiment of the present disclosure.

Figure 1:
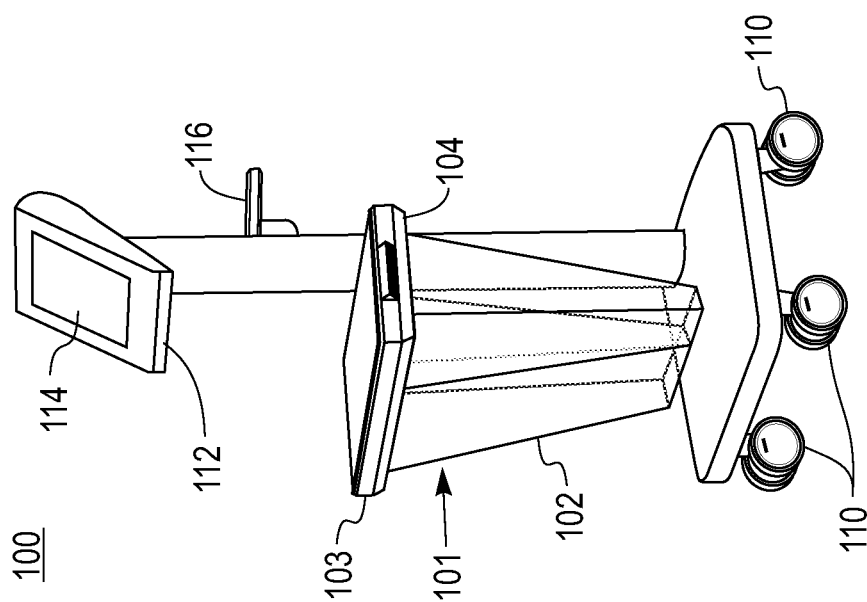

Referring to FIG. 1, an example of a surgical object and fluid monitoring system (Monitor System) 100 is shown, according to various embodiments of the present disclosure.

The Monitor System 100 supports a container 101 that can receive and contain surgical objects, including but not limited to sponges and fluid-retaining sponges. The container 101, according to various embodiments is disposable. The container 101, according to various embodiments is constructed of lightweight plastic or polymer materials and film. The container 101, according to the present example, includes a container main body 102 that is directly mechanically coupled to a container top 103. According to various embodiments, the container main body 102 and the container top 103 are mechanically coupled in a fluid-tight seal.

The container main body 102, according to the present example, comprises a flexible film bag 102 that can be easily compressed and collapsed into a small volume adjacent to the underside of the container top 103. When the container top 103 is supported in a horizontal orientation, as shown in FIG. 1, the flexible film bag 102 easily falls down from the top 103 (by the force of gravity) thereby fully expanding and conforming to its fully expanded open shape, as shown in FIG. 1. The container main body 102 is therefore self-expanding from its compressed volume shape to its fully expanded ready-to-use shape, by the force of gravity.

In the present example, as illustrated in FIG. 1, the container 101 is supported by its top 103 that is securely supported by an optical sensor ring (OSR) 104 of the Monitor System 100. The OSR 104 is mechanically coupled to, and supported by, a vertical spine 106 of the Monitor System 100. The flexible bag 102 falls down from the supported top 103 by the force of gravity. The empty flexible bag 102, when supported by the OSR 104, fully expands to its open shape ready-to-use with the Monitor System 100.

As shown in the example of FIG. 1, the flexible bag 102 has a shape that tapers from wider cross-section about the top 103 to narrower cross-section towards the bottom of the bag 102. This container 101 is easy to transport and store, especially with the container main body 102 compressed/collapsed to a reduced volume shape adjacent to the underside of the top 103.

For example, the empty, compressed, container 101 can be easily stored in a sealed storage package (not shown) that keeps the container 101 sanitary and ready to use in a clean room such as a surgical operating room. Then, when a user (e.g., a surgical nurse or assistant) opens the sealed storage package and removes therefrom the container 101, by only holding the top 103 by its handles (as shown in FIG. 3), the container self-expands to its full ready-to-use shape by the force of gravity. The user does not have to manipulate the container main body 102 to cause the container 101 to fully expand to its full open shape ready to use. The user can support the container top 103 in a horizontal orientation (e.g., by holding the top 103 by its handles in a natural gesture similar to carrying a tray) and the empty container main body 102 will self-expand (e.g., fully expand to its open ready-to-use shape). This container 101 design provides a user friendly container product that is easy to store and transport, easy to extract out of the OSR for disposal of the container and its content, and easy to dispose of after use.

As shown in FIG. 1, the Monitor System 100 comprises a vertical spine 106 that is maintained in a substantially vertical orientation and supported by a base 108 of the Monitor System 100. The base 108 may include, according to various embodiments, several wheels 110 that allow the user to easily move (i.e., push-pull) the Monitor System 100 to a desired location for use. A handle 116 extends from the vertical spine 106 such that a user of the Monitor System 100, for example, can grab the handle 116 and thereby pull or push the Monitor System 100 on its wheels 110 to a desired location. FIG. 2 shows a user with a hand 208 grabbing the handle 116 of the Monitor System 100.

As shown in FIG. 1, the Monitor System 100 includes controller unit 112 that is supported at the top of the vertical spine 106. The controller unit 112, according to the present example, includes a touch screen liquid crystal display 114 that provides a user interface for a user of the Monitor System 100. Any type of touch screen display technology may be used in the Monitor System 100, as may be desired for various applications.

With reference to FIG. 2, the Monitor System 100 is shown with the container 101 having received an object, such as a fluid filled sponge, 204 within an internal compartment of the container 101. As shown in the example illustrated in FIG. 2, there are two fluid filled sponges 204 that have been received within the internal compartment of the container 101. One of the sponges 204 includes at least one RFID device 205 incorporated therein. Objects, such as sponges, 204 that include RFID devices 205 can be monitored (e.g., interrogated) by RFID communication circuitry (e.g., at least one RFID reader) in the Monitor System 100 to obtain information associated with each such particular object 204 and its at least one RFID device 205, as will be discussed in more detail below. The container main body 102 can include one or more compartments that each can receive and contain objects, such as fluid filled sponges, that are dropped into the container 101 through one or more ports or openings 206 at the top 103 of the container 101.

A top lid 202 may be used to cover the one or more openings 206 on the container top 103 after the container has received one or more objects 204 and its use has been completed. The top lid 202 will cover the one or more openings 206 and, according to certain embodiments, will create a fluid-tight seal with the container top 103. This facilitates removal of the container 101 from the Monitor System 100 as well as disposal of the container 101. The container 101 with the top lid 202 covering the one or more openings 206, and optionally creating a fluid-tight seal at the container top 103, securely contains the object 204 in a compartment inside the container 101. With the object 204, such as a fluid-filled sponge, being securely contained and sealed within the container 101, the container 101 can be easily removed from the Monitor System 100 and disposed accordingly without concern for leakage of bio-contaminated and/or hazardous objects or fluids from the container 101.

As shown in FIG. 3, the user 302 can hold the container 101 by the container top 103, such as by handles on either side of the container top 103. The container main body (e.g., a flexible bag) 102 fully expands to its ready-to-use shape and the empty container 101 can easily be lowered 304 by the user 302 onto the optical sensor ring 104 which then acts as support for the container 101. The arrow 304 indicates how the user 302 lowers the container 101 into the center opening of the optical sensor ring 104. Of course, the reverse procedure can be used to remove the container 101 from the OSR 104. By lifting the container 101, e.g., a used container 101 containing one or more objects 204, the user 302 can remove the container 101 from the OSR 104 and from the Monitor System 100. The user can then be safely and conveniently dispose of the removed container 101.

It should be noted that while the optical sensor ring 104 is shown as a continuous rigid ring structure in the present example, according to other embodiments the optical sensor ring 104 could have a hinged portion (not shown) that is rotatable away from the other portions of the OSR 104. For example, a left portion or a right portion of the OSR 104 could be the hinged rotatable portion. The hinged rotatable portion could be secured (e.g., using a locking or latching device) to the remaining structure of the OSR 104 to form the continuous ring shape of the OSR 104. When a container 101 is full of objects 204, and its total weight may be significant, the user 302 could avoid having to lift the full container 101 from the OSR 104. By opening the locking or latching device at the hinged rotatable portion, the user can hold the handles at the top 103 of the full container 101 and remove it from the OSR 104 by lateral movement—to the left or right of the OSR 104. The user 302 would not have to lift the full container 101 higher than its current level while supported by the OSR 104.

According to the example of the Monitor System 100 shown in FIG. 3, one or more RFID communication circuitries 305, 307 (e.g., at least one RFID reader) in the Monitor System 100 are located, for example, and not for any limitation, at about or in the OSR 104. More specifically, for example, as shown in FIG. 3 a first RFID communication circuitry 305 can be located at a back portion 608 (see also FIG. 6) of the OSR 104 and a second RFID communication circuitry 307 can be located at a front portion 610 of the OSR 104. In this example the first and second RFID communication circuitries 305, 307, are located at, or adjacent to, an inner surface 606 of the OSR 104 in proximity to a center opening of the OSR 104 that is defined by the inner surface 606.

It should be noted that the locations discussed above are for presenting one non-limiting example, and RFID communication circuitry may be located at one or more suitable locations in the Monitor System 100. For example, one or more RFID communication circuitries can be located at, or in, the vertical spine 106, in addition to the one or more RFID communication circuitries 305, 307 (e.g., at least one RFID reader) located at or in the OSR 104. The RFID communication circuitries at or in the vertical spine 106, according to this example, are vertically located arranged along the vertical spine 106 and in proximity to one or more levels of a container 101, while vertically supported by the OSR 104, from the top 103 of the container 101 along the container main body 102 to the bottom of the container 101.

In this arrangement, for example, objects 204 including at least one RFID device 205 can be monitored (e.g., via the information in the object's respective RFID device 205) entering the top 103 of the container 101 (e.g., monitored by the one or more RFID communication circuitries 305, 307). The objects 204 can be further monitored to be placed inside the container 101 at one or more levels vertically along the container 101 from the top 103 of the container 101 along the container main body 102 to the bottom of the container 101. Many different locations of RFID communication circuitry in the Monitor System 101 are anticipated suitable for various embodiments of the present disclosure.

Continuing with the example shown in FIG. 3, the one or more RFID communication circuitries (e.g., the at least one RFID reader) 305, 307, can communicate via short range communications with RFID devices 205 of objects 204 that are in the near vicinity to the RFID communication circuitries 305, 307, such that, for example, information associated with each such RFID device 205 can be obtained by the Monitor System 100. Objects, such as sponges, 204 that include RFID devices 205, when in proximity to the at least one RFID reader 305, 307, can be quickly monitored (e.g., interrogated) by the at least one RFID reader 305, 307, and thereby information associated with each such object and its RFID device 205 can be obtained by the Monitor System 100.

Additionally, the approximate location of the particular object 204 including the at least one RFID device 205 can be determined relative to a container 101 that is supported by the OSR 104. For example, an object 204 including at least one RFID device 205 can be quickly monitored (e.g., via the information in the object's respective RFID device 205) entering an opening 206 at the top 103 of the container 101. That is, in the current example, while the object 204 is being placed into the container 101 the RFID device 205 can be quickly monitored (e.g., interrogated) by the one or more RFID communication circuitries 305, 307 in proximity to the at least one opening 206 at the top 103 of the container 101. It should be noted that, according to certain embodiments of the present disclosure, interrogation by the one or more RFID communication circuitries 305, 307, in proximity to an object 204 including at least one RFID device 205 while being placed in the at least one opening 206 can be a sufficiently reliable mechanism to detect a time when the object 204 is placed into the at least one opening 206 at the top 103 of the container 101. For example, in the certain embodiments, the reliable detection of the time when the object 204 is placed at the at least one opening 206 (e.g., placed at a detection region in the container 101) by using RFID interrogation may not need to additionally utilize other detection mechanisms, such as using other beam sensors/detectors in the OSR 104 as discussed herein and particularly with reference to FIG. 14.

According to the example, the object 204 can be additionally monitored to be placed inside the container 101 at one or more levels vertically along the container 101 from the top 103 of the container 101 along the container main body 102 to the bottom of the container 101. That is, in this example, one or more RFID communication circuitries are located at, or in, the vertical spine 106, in addition to the one or more RFID communication circuitries 305, 307 (e.g., at least one RFID reader) located at or in the OSR 104. The one or more RFID communication circuitries located at, or in, the vertical spine 106 are arranged along the vertical spine 106 and in proximity to one or more levels of a container 101, while the container 101 is vertically supported by the OSR 104. The object 204 and its RFID device 205, while placed inside the container 101, can be monitored being in proximity to the particular one or more RFID communication circuitries located at, or in, the vertical spine 106 while the object 204 is at one or more levels in the container 101. The one or more RFID communication circuitries at, or in, the vertical spine 106 can operate to quickly interrogate/monitor the proximately located RFID device 205 while the object 204 drops in the container 101 to one or more levels inside the container 101 from the top 103 along the container main body 102 to the bottom of the container 101. This additional monitoring of the object 204 placed at the at least one opening 206 and entering inside the container 101 provides additional affirmative and reliable confirmation that the object 104 has been placed inside the container 101.

As shown in FIG. 4, after the container 101 is placed through the center opening of, and supported by, the OSR 104, the top lid 202, according to one example, can be rotated up-and-to-the-rear of the container top 103, as indicated by the arrow 402. According to certain embodiments, the top lid 202 then remains vertically supported by the vertical spine 106, as shown in FIG. 4. Optionally, a small magnet may be embedded in the top lid 202. When the top lid 202 is resting vertically against the vertical spine 106 the top lid 202 is removably secured to the vertical spine 106 by magnetic force between the small magnet in the top lid 202 and a metallic surface of the vertical spine 106. A user can, as necessary, pull and remove the top lid 202 from the vertical spine 106 and rotate the lid 202 back onto the top surface of the container top 103.

The top lid 202 provides a splash guard for any fluids that may be splashed by fluid-containing objects being placed into the container 101 through the one or more openings 206. Additionally, the container lid 202 can include writing or symbols, as illustrated in FIG. 4, to visually help guide the user to locate the appropriate opening 206 to drop an object into the container 101. As shown in FIG. 4, there are two compartments within the container 101. One compartment holds smaller objects (e.g. small fluid-containing sponges), while the second opening 206 is for a second compartment in the container 101 that holds larger objects (e.g. large fluid-containing sponges). In this way, according to the present example, the container 101 can be used to not only contain objects 204, but also to help sort these objects in the corresponding compartments. The objects 204 are sorted by attributes of each group of objects such as by size, thickness, or other dimensions, of sponges being used in a surgical procedure. According to various embodiments, other attributes of objects 204 can be used for sorting the objects 204 in the different compartments within the container 101.

Figure 5:
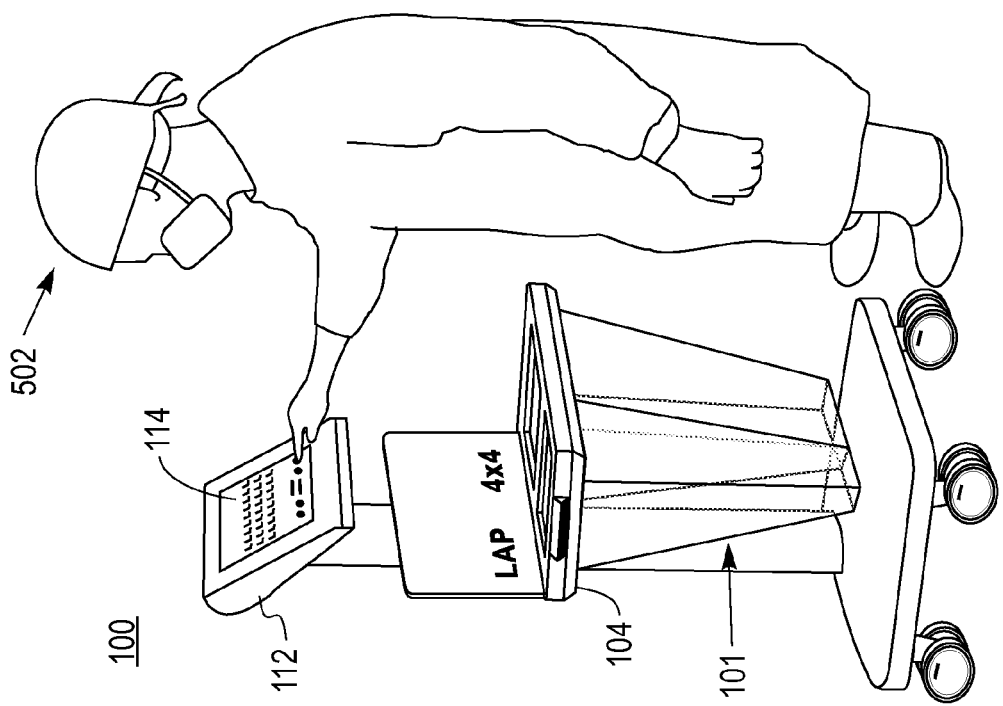

Referring to FIG. 5, the user 502 can touch the touch screen 114 of the Monitor System 100 to communicate information with the Monitor System 100. For example, the user 502 can use a finger of the hand, or a stylus, to touch locations on the touch sensitive surface of the touch screen 114. In this way, the user 502 can communicate commands and/or data to the Monitor System 100, and optionally configure parameters of the Monitor System 100, in accordance with a particular implementation of the Monitor System 100.

The user 502 can enter configuration information into the Monitor System 100 to let the Monitor System 100 know, for example, how many compartments are in the container 101 and the types of objects and their attributes that may be expected to be placed in these compartments. Additionally, the user 502 can provide information to the Monitor System 100 to inform the Monitor System 100 of how many objects to expect to be placed in each of the compartments in the container 101.

The touch screen 114 provides a user interface that not only receives information from the user 502, but also displays information to the user. In this way, the user 502 can be informed of certain events that occur with the Monitor System 100 and certain conditions experienced by the Monitor System 100. For example, the touch screen display 114 can display a count of the number of objects, such as fluid-filled sponges, that have been deposited in each of the compartments in the container 101. Additionally, for example, the touch screen display 114 can display to the user 502 the approximate amount of fluid by weight (or by calculated volume) that has been accumulated in the compartments of the container 101.

Once the Monitor System 100 has been configured and is ready to use, the user places each object (e.g., such as a fluid-filled sponge removed from a patient during a surgical procedure) at one of the one or more openings 206 in the top 103 of the container 101, and then allows the object to drop through the particular opening 206 and down into a receiving compartment within the container main body 102.

Each of the one or more openings 206, according to the present example, comprises a funnel shape with a gradual inward sloping surface from the top surface of the container top 103 down toward the inside of a compartment in the container main body 102. This funnel shape helps guide the objects being placed at the opening 206 into the particular compartment of the container 101. Also, this funnel shape more reliably places the falling object at a generally central region of the opening 206. By dropping the object 204 down from a central region of the opening 206, a plurality of sensors in the OSR 104 just below the opening 206 can more reliably sense/detect the falling object, as will be discussed below.

One or more sets of emitters located along an inner surface of the OSR 104 emit respective one or more beams (e.g., infrared "IR" beams and/or optical beams) across a central opening of the OSR 104 aimed at respective one or more sensors that are compatible with the sensors and beams and located along an opposing inner surface of the OSR 104. For example, a first group of alternating optical emitters and optical sensors may be located along an inner surface of a rear portion of the OSR 104.

Additionally, a second group of alternating optical sensors and optical emitters (opposing the first group of optical emitters and sensors) may be located along an inner surface of a front portion of the OSR 104. Each optical emitter is matched to an opposing optical sensor to create an optical beam that traverses across the center opening of the OSR 104.

A detection region is formed by a plurality of optical beams spanning across the front portion and rear portion of the center opening of the OSR 104. The detection region is just below the end of each funnel shaped port or opening 206 in the container 101.

To facilitate the optical beams traversing across the center opening of the OSR 104 while the container 101 is supported on the OSR 104, according to various embodiments, the construction and material of the walls of the container main body 102, at least in the detection region just below the funnel shaped opening(s) 206, are optically transparent over the relevant wavelength and frequency range of the Infra-Red (IR) optical beam, e.g., over IR wavelength and frequency range of the optical beam sensed by the sensor.

Optionally, the material and construction of the walls of the container main body 102, at least in the detection region just below the funnel shaped opening(s) 206, can be optically transmissive or optically transflective, at the relevant wavelength and frequency range of the optical beam. This material and construction is designed to enhance the ability of each of the optical beams emitted from an emitter device at the inner surface about the ring center opening of one portion of the OSR 104 to reach and be detectable by the matching sensor device at the opposing inner surface about the ring center opening of another portion of the OSR 104.

For example, according certain embodiments, Dupont Corporation makes a clear polyethylene film product called CLEAR that provides optical qualities suitable for use in the construction and material of the walls of the container main body 102, at least in the detection region just below the funnel shaped opening(s) 206. Another desired aspect of the construction of the walls of the container 101, at least in the detection region just below the funnel shaped opening(s) 206, is that the walls traversed by an optical beam be oriented substantially perpendicular to the axis of the optical beam. This perpendicular wall orientation relative to the optical beam axis enhances the amount of optical energy that passes through the wall and thereby enhances the ability of the beam to reach and be detectable by the corresponding optical sensor device.

Therefore, in view of the discussion above, an object (e.g., a sponge) placed at the opening 206 while dropping into the corresponding compartment in the container 101 will have to pass through the detection region covered by the one or more optical beams (e.g., IR beams). The one or more beams traverse across this detection region such that when each object is dropped into an opening 206 of the container 101 at least one beam is broken by the falling object while the object passes the detection region. The break of the beam is sensed by the respective optical sensor and a beam break signal is sent from the optical sensor to a processor/controller in the Monitor System 100, to indicate that an object has been dropped into the particular port opening 206.

A more sophisticated approach to sensing and monitoring an object being dropped through a detection region is provided here according to various embodiments. A plurality of beams (time and spatially multiplexed), between the inner surface of the rear portion of the OSR 104 and the inner surface of the front portion of the OSR 104, are spaced apart a known distance from each other in the detection region. After at least one beam break is detected by the processor/controller the sensors and the processor/controller can continuously monitor the beam break(s) while the object continues to fall past the detection region. The beam-break-sense monitoring, for example, can be repeated every 10 milliseconds until all of the optical beams are sensed again (i.e., no beam breaks detected). The spatial location of the beam break(s) would signify the specific port (i.e., opening 206) at the top of the container through which an object enters.

Key objectives of various embodiments include, but are not limited to, reliably sorting the object types (in this example two different sponge types correspond to two respective openings 206, i.e., two ports, at the top of the container); providing a valid count of the appropriate object type thrown in the container (eliminating/minimizing false positives); and estimating the fluid content in each such object.

The sorting of object type, according to the present example, is done by providing two ports on top of the container, each port identified with a specific sponge type (this has been described somewhat elsewhere in the present disclosure). Each port is blanketed by a set of IR beams (see, for example, FIG. 14), and each set of IR beams is multiplexed, scanned and monitored by the processor/controller. The processor/controller can then identify the sponge type that was dropped based on which port the IR beam(s) was interrupted.

In order to achieve a reliable object (e.g. a used sponge) count (and eliminate false positives), the key is in the use of an "intelligent" algorithm that uses information from the sensor beam breaks and the incremental weight change measurement (such as using a load cell that will be more fully described below) when a sponge (or object) is thrown in the container through one of the ports. Namely, with general reference to FIGS. 14, 15, and 16, which will be discussed in more detail further below, when an object passes through the beams 1402, 1404, a beam first "breaks" and then "unbreaks" at the tail-end of the passage of the object. The object will fall to the bottom of the container within a maximum time, $\Delta Td$-max 1512, and an incremental weight change, $\Delta W$ 1610 will be measured at $\Delta TW$ 1606 relative to the baseline reference weight established at TBB 1508—when the beam "unbreaks" after a "break"). So, a valid count is recorded only if $\Delta W$ 1610 is valid and it is within the pre-stored weight range of fluid content (i.e., between zero to fully saturated sponge weight). The following three exceptions should be noted, however.

First, if the beam is broken (e.g., by inserting one's fingers through port or sponge stuck at the port), no count will be registered because either the beam is broken and no weight change—or—the beam is continuously broken with or without weight change. Either case would violate the rules for a valid count, as has been described above.

Secondly, if the beam is broken properly (with the "break" and "unbreak" sequence in place) but the incremental weight $\Delta W$ 1610 is outside the prescribed range, the count is considered invalid.

Figure 16:
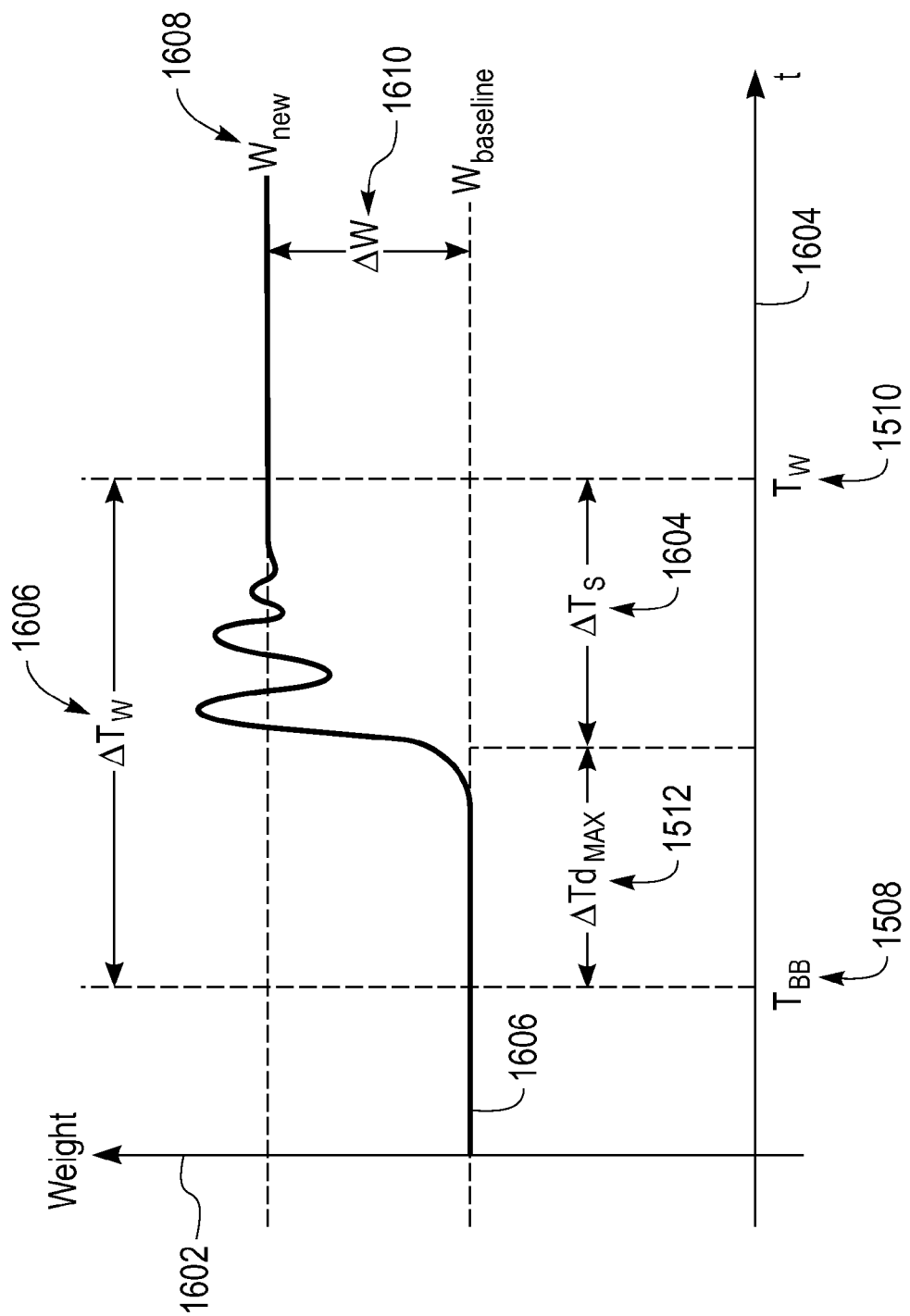
FIG. 16 is a timing diagram illustrating a weight signal from a load cell vs. time, according to the present disclosure.

Third, if a foreign weight is placed on the container (e.g. tray, tongs, etc.), the temporary or permanent increase of the overall weight of the container due to the foreign weight will not hamper the measurement of the actual incremental weight $\Delta W$ 1610 of a sponge (object) that has traversed the optical sensors; hence the sponge will be counted as valid. Note that $\Delta W$ 1610 is a relative measurement as shown in FIG. 16.

Once a valid sponge (object) is detected in the container and counted based on the above rules, then for each $\Delta W$ 1610 measured the incremental fluid content of the container is calculated by subtracting from $\Delta W$ 1610 the pre-stored tare weight (Wtare) of the sponge type. This incremental fluid content is accumulated to the running total Fluid count maintained by the Monitor.

The fluid content of the object extracted/calculated from its incremental weight $\Delta W$ 1610 is used to accumulate the total fluid count. Hence, any extraneous weight placed on the container (or removed via evaporation of fluid from the container) would not, and should not, factor into the accumulated total fluid count maintained by the Monitor.

Now, continuing with the description of the example Monitor System 100, and with particular reference to FIGS. 4 and 5, a plurality of optical emitter beams blanket the region just below the one or more openings 206 at the top 103 of the container 101. The one or more optical emitter beams pass from a first inner side of the OSR 104, through the opposing walls of the container main body 102, and across to and below the one or more funnel openings 206, to one or more optical sensors located in an opposing second inner side of the OSR 104. The one or more optical beams, therefore, traverse the ring center opening from across opposing inner sides of the container main body 102 just below the funnel shaped openings 206 of the container top 103. The optical beams, according to various embodiments, pass through the walls of the container main body 102, at least about the detection region where the optical beams traverse the ring center opening of the OSR 104 from across opposing inner sides of the container main body 102.

After the Monitor System 100 detects that an object has been dropped into the compartment within the container 101, e.g. by detecting one or more beams between optical emitters and optical sensors have been broken, the Monitor System 100 can additionally monitor the incremental weight change due to the object that has been dropped in the container 101. After an object is dropped into the compartment of the container 101, the object after traversing one or more of the optical beams in the detection region of the container 101, will further drop and make contact either 1) with the bottom of the container main body 102 (corresponding to an empty compartment of the container 101), or 2) with the object(s) already resting on the bottom. When the object drops inside a compartment of the container 101 and delivers its incremental weight to the container 101, such as when the object reaches the bottom of the container 101, the object's weight can be established by the Monitor System 100.

According to certain embodiments, the Monitor System 100 includes an electronic load cell mechanically coupled to the OSR 104 that supports the container 101, and thereby senses the weight of the container 101 and its contents. Thus, the load cell can provide a signal that indicates the incremental weight of the object that has been dropped into the container 101, as the weight is transferred from the container 101 to the OSR 104, and thereby transferred to the electronic load cell in the Monitor System 100. In this way, the Monitor System 100 detects an object being dropped into the container 101 and establishes the incremental weight of the object that was just dropped in the container 101.

Based on information in the Monitor System 100, such as information that the user 502 configured in the Monitor System 100 by using the touch screen display 114, the attributes of the object expected to be dropped into a particular compartment in the container 101 are known to the Monitor System 100. In the case where the object 204 in the container 101 is carrying fluid, the additional weight of the fluid in the object 204 will also be part of the total weight of the dropped object that is detected by the load cell and the Monitor System 100. By subtracting the known approximate weight of the object 204 before being filled with fluid from the total weight of the dropped object 204 (e.g., which is fluid filled) the Monitor System 100 can establish the weight of the fluid in the object that was dropped into the container 101.

This incremental weight of fluid can additionally indicate a certain volume of fluid when the type of fluid is known. For example, for blood filled sponges that are dropped into the container 101 the Monitor System 100 calculates, based on the cumulative measured weight of the blood contained in the sponges, the approximate amount of total volume of blood removed (via the sponges) from the patient during a surgical procedure. That is, the weight of the blood carried in the sponges can be used to approximate the cumulative volume of the blood loss.

By information being displayed to the user via the touch screen display 114, for example, the Monitor System 100 can inform the user of the total count of objects being dropped in the container 101, the type of objects sorted in a compartment in the container 101, and an estimation of the total volume of fluid loss (e.g., blood loss) from a patient during surgical procedure. That is, according to various embodiments, the volume estimate would be based on the weight of the fluid carried within the objects being deposited into the container 101. One or more controllers (or processors) in the Monitor System 100 can be used to monitor the objects being dropped in the container 101 and then calculate and display via the touch screen display 114 valuable information to the user, such as the count of the total number of objects being dropped into the container 101, sorted by type of object that is dropped into the container 101, and a calculated estimate of fluid loss volume from a patient as indicated by the weight of the fluid in the fluid-filled objects 204 being dropped into the container 101.

Figure 6:
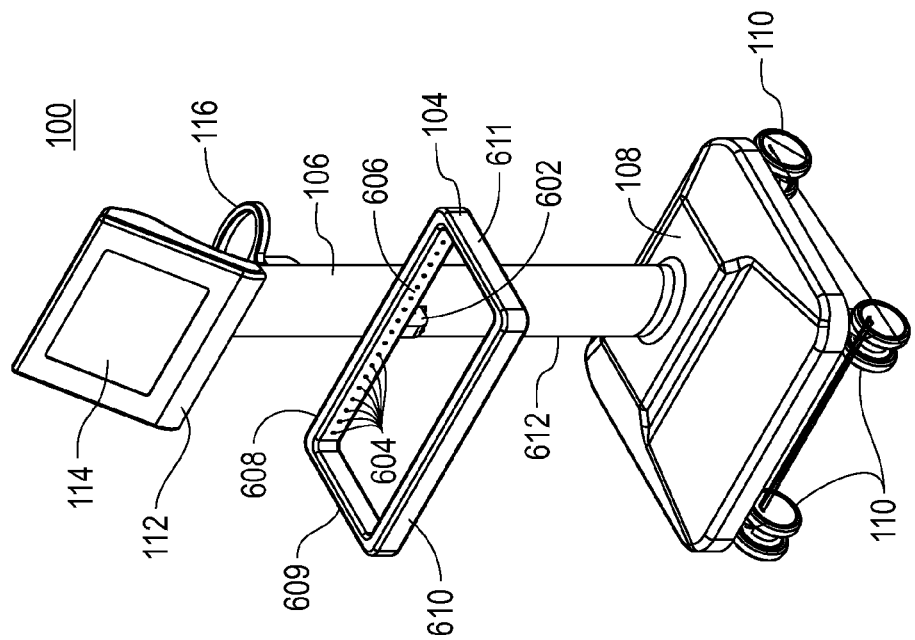
FIGS. 6 and 7 are perspective views of an example of a monitoring system and its internal components, according to the present disclosure.

FIG. 6 is a more detailed perspective view of the Monitor System 100 shown in FIG. 1, according to the present example. The Monitor System 100 is shown without the container 101. The vertical spine 106 is supported by the base 108 which, according to the present example, includes a plurality of wheels 110. The vertical spine 106 supports the controller unit 112 at the top of the vertical spine 106, as shown. The handle 116 extends outward from the vertical spine 106 and is secured to the vertical spine 106. When the user grabs the handle 116 with a hand 208 (see FIG. 2) a processor/controller within the controller unit 112 detects the user's hand 208 making contact with the handle 116.

For example, a capacitive sensor circuit can be electrically coupled with the handle 116 thereby sensing when the user's hand 208 makes contact with the handle 116. A variable frequency circuit may be electrically coupled with the handle 116 in a capacitive electrical coupling arrangement such that the user's hand 208 would change the capacity of the variable frequency circuit when touching the handle 116. A first frequency of the circuit would indicate to the internal processor/controller that the handle 116 is not in contact with the user's hand 208, and a second frequency would indicate that the user's hand 208 is in contact with the handle 116. This is just one example of sensing when the user's hand 208 makes contact with the handle 116. There are many different ways that the Monitor System 100 can detect a user's hand 208 being in contact with the handle 116.

When the processor/controller detects that the user's hand is in contact with the handle 116 (e.g., grabbing the handle 116), the processor/controller, according to various embodiments, controls an electro-mechanical breaking system at the plurality of wheels 110 such that when the user's hand 208 is grabbing the handle 116 the wheel's brakes are released thereby allowing the user to freely move and roll the Monitor System 100 on the floor. Alternatively, when the user's hand 208 releases from the handle 116, the processor/controller detects this event and immediately applies the braking system to the plurality of wheels 110, thereby locking in place the Monitor. According to standard practices, the location of the Monitor should be spaced no closer than 12 inches from the operating room table's sterile field. The immediate response by the processor/controller to the user's release of the handle 116 facilitates precise locking in place the Monitor at the required spacing distance.

Optionally, besides the handle 116 being a point of contact for the user's hand 208 to release the braking system from the plurality of wheels 110, a user's contact anywhere on the outer body of the Monitor System 100 may create a sensing event where the processor/controller could detect the contact and thereby the intention to release the braking system from the plurality of wheels 110. For example, the vertical spine 106 includes an outer housing 612 that may include conductive material (e.g. metallic material) that would be part of a variable frequency sensor circuit such that when a user's hand 208 makes contact with the outer housing 612 it varies the frequency of the variable frequency circuit. The processor/controller in the Monitor System 100 would detect this event and immediately release the braking system from the plurality of wheels 110 allowing the Monitor System 100 to be easily moved across the floor with the rolling wheels 110.

As soon as the user's hand 208 is removed from the contact of the outer surface 612 of the vertical spine 106, the braking system is immediately applied to the plurality of wheels 110 thereby locking the wheels 110 making the Monitor System 100 immovable. As may be appreciated, other outer surfaces of the Monitor System 100 could similarly be electrically coupled with a sensor circuit such that the processor/controller could detect a contact event with the user's hand 208 and utilize the occurrence of this event to release the braking system from the wheels 110, or when the user's hand 208 is removed from the other outer surface on the Monitor System 100 to immediately apply the braking system to the wheels 110.

According to the present example, the optical sensor ring (OSR) 104 is supported by a support extension 602 from the vertical spine 106. The OSR 104 has a back ring portion 608 and a front ring portion 610, as well as a left ring portion 609 and a right ring portion 611, that in combination form the OSR 104 with a ring center opening within the four portions 608, 610, 609, 611. The ring center opening is defined by the inner surface 606 of the OSR 104.

A plurality of optical sensors matched to optical beam emitters 604 are located along the inner surface 606 of the OSR 104. Each optical sensor in the plurality 604 is matched with an opposing optical beam emitter in the plurality 604 along the inner surface 606 of the OSR 104, e.g., along the inner surface 606 of the back portion 608 and the front portion 610 of the OSR 104. That is, according to this example, an optical emitter is matched with an optical sensor located on the inner surface 606 opposing each other between the back portion 608 and the front portion 610 of the ring 104. This arrangement of optical sensors and optical emitters 604 creates a grid of one or more beams traversing from the optical emitter to the optical sensor across the ring center opening of the OSR 104.

According to one embodiment, the plurality 604 has alternating optical sensors and optical emitters located along the inner surface 606 of the back portion 608 of the OSR and a matching plurality 604 of opposing optical sensors and optical emitters along the inner surface 606 of the front portion 610 of the OSR 104. The plurality 604 of optical emitters and optical sensors along the inner surface 606 of the back portion 608 and the front portion 610 of the OSR 104 can be activated in one or more patterns of optical beams traversing across the ring center opening of the OSR 104.

One example of a pattern for activating the plurality 604 of optical emitters and optical sensors could be a serial activation of optical emitters and opposing optical sensors from the rear portion 608 and the front portion 610 of the OSR 104, forming a moving curtain of serially activated beams (e.g., IR light beams) that can be used in the Monitor System 100 to detect when an object traverses through the ring center opening of the OSR 104. Another example pattern could be a static set of optical beams aimed between optical emitters and opposing optical sensors located along the inner surface 606 of the rear portion 608 and the front portion 610 of the OSR 104.

A processor/controller in the Monitor System 100 can selectively energize pairs of the plurality of optical emitters and matched optical sensors across the ring center opening to detect objects being placed within the ring center opening of the OSR 104. One or more examples of this arrangement in use of matched opposing optical emitters and optical sensors along the inner surface 606 of the OSR 104 will be discussed in more detail below.

With reference to FIGS. 6 to 12, a more detailed description of the electro-mechanical structure supporting the OSR 104 at the Monitor System 100 will be discussed below. The OSR 104 is supported by a support extension 602 that extends from the inside of the vertical spine 106 through an opening in the outer housing 612 of the vertical spine 106. The support extension 602 rigidly supports the OSR 104 and mechanically couples the OSR 104 to a load cell push rod 702 within the vertical spine 106. For example, two bolts (see FIGS. 9, 10, and 12) mechanically secure the support extension 602 to the load cell push rod 702. The support extension 602 may also be referred to as a ring mount 602.

The load cell push rod 702 is mechanically fixed to the ring mount 602 and to a channel impactor block 704, as better shown in FIGS. 7, 9, 10, and 12. The channel impactor block 704, according to various embodiments, is constructed of impact absorbing material such as plastic, polypropylene, or the like. The push rod 702 is mechanically coupled to a load cell 706 inside the base 108 of the Monitor System 100. The load cell 706 is mechanically fixed to a surface of the bottom portion 708 of the base 108. A right securing block 710 and a left securing block 712, a backbone structure 902 (not shown in FIG. 7, and better shown in FIGS. 9-12), that supports the vertical spine 106 on the bottom portion 708 of the base 108. The backbone structure 902 will be discussed in more detail below.

A pushrod flexure 714 is mechanically coupled to the top of the pushrod 702 and to a securing plate 716 that is mechanically coupled to the backbone structure 902 inside the spine 106. The pushrod flexure 714 acts as a tensioning spring force element on the pushrod 702 keeping the pushrod 702 vertically aligned and in contact with the load cell 706. The spring force of the flexure 714 on the pushrod 702 under normal operations is very minimal, adding very little if any downward force onto the load cell 706, while maintaining the pushrod 702 vertically aligned and in contact with the load cell 706. The flexure 714 comprises a thin flat metal structure, such as 8 thousands to 12 thousands of an inch thick. The flexure 714 typically moves with the pushrod 702 movement approximately one thousands of an inch to two thousands of an inch, and provides a negligible spring force to the pushrod 702.

When downward force is imparted onto the OSR 104 (e.g., when the container 101 is supported within the ring center opening of the OSR 104, and an object is deposited in the container 101), this downward force is transferred through the ring mount 602 and the pushrod 702 to the load cell 706. The pushrod 702 normally moves the load cell 706 (typically comprising a cantilever mechanical system) just thousands of an inch or less to impart the downward force. The flexure 714 does not impart much if any force onto the load cell 706. So the combination of the OSR 104, ring mount 602, pushrod 702, and load cell 706, comprises a very accurate weight measurement system.

The downward force imparted by the pushrod 702 on the load cell 706 includes the incremental weight of the object being dropped in the container 101. This incremental weight of the object is then sensed via the load cell 706. The load cell 706 provides an electrical information signal to a processor/controller in the Monitor System 100. It should be noted that according to the present example, the load cell 706 is located inside the base 108 of the Monitor System 100. This lowers the center of gravity and enhances the stability and security of the Monitor System 100, to avoid tipping and bumping over during use and/or transport. However, according to other embodiments of the present disclosure the load cell 706 could be located above the pushrod 702, such as in the controller unit 112, and sense the force imparted onto the pushrod 702 by the OSR 104.

Figure 8:
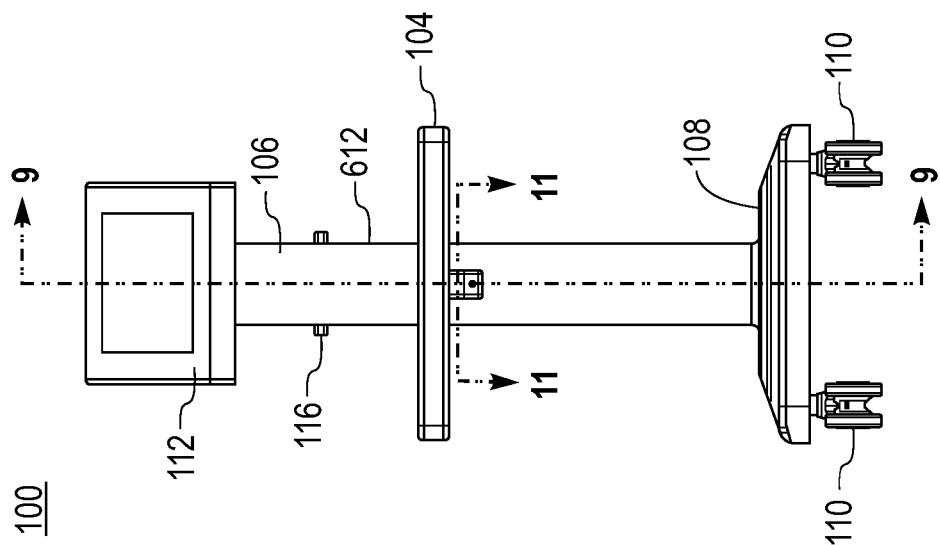
FIG. 8 is a front planar view of the monitoring system shown in FIGS. 6 and 7, according to the present disclosure.
Figure 7:
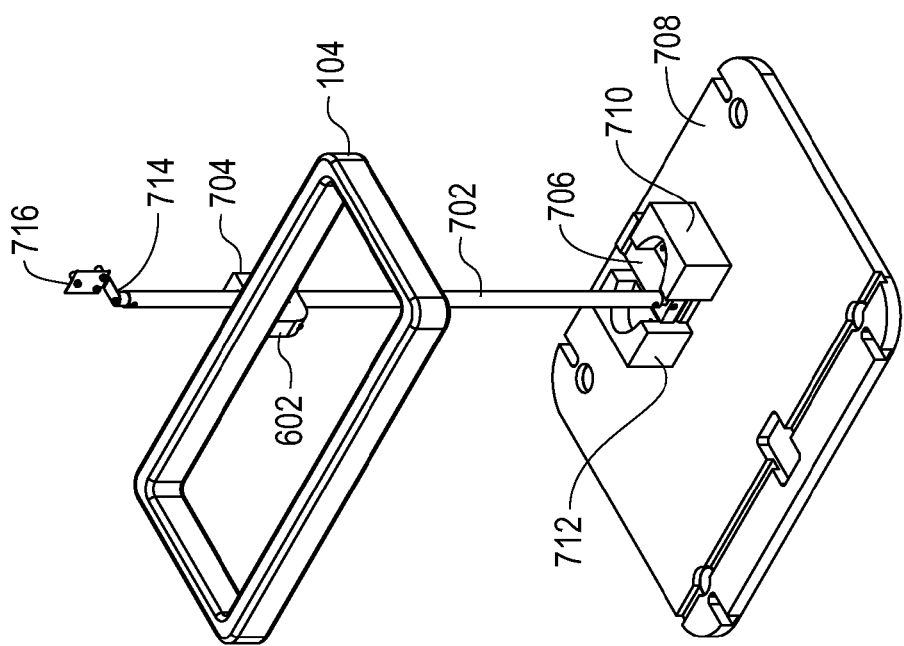
Figure 10:
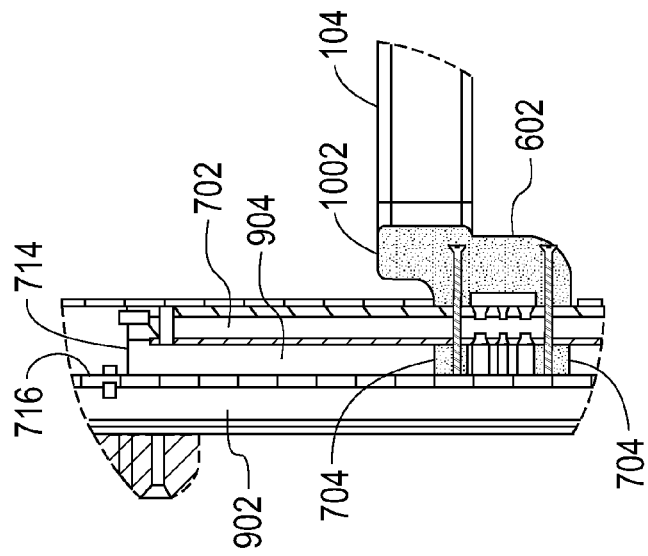
FIGS. 9 and 10 are cross-sectional side views of the monitoring system shown in FIG. 8.
Figure 9:
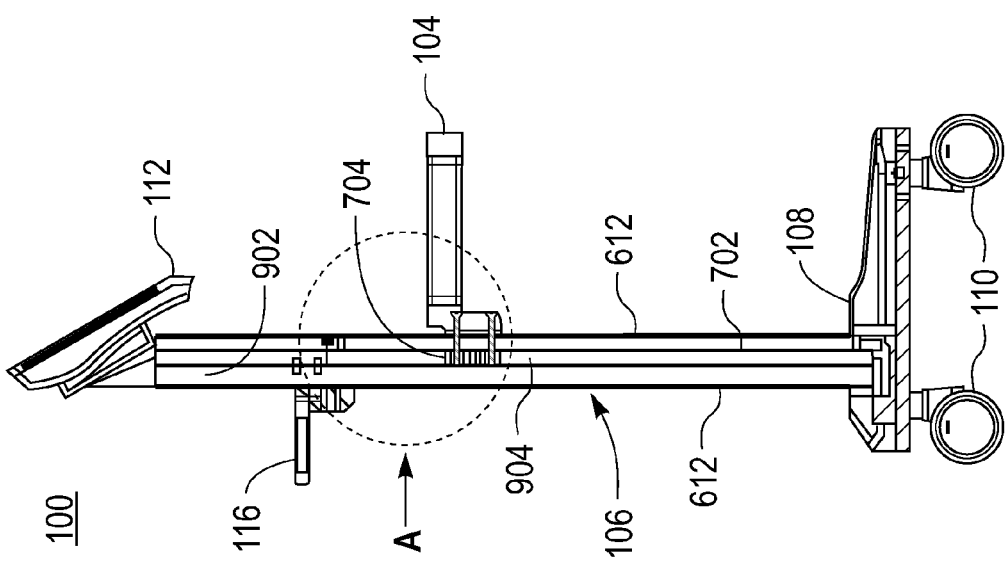
Figure 11:
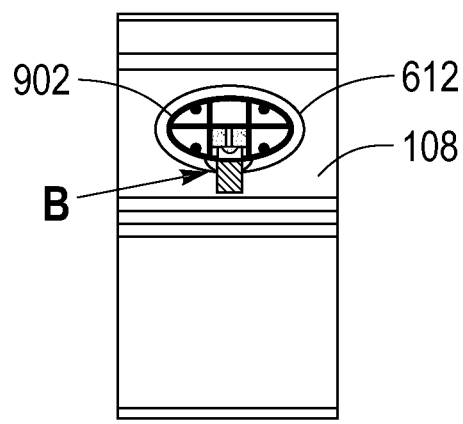
FIGS. 11 and 12 are cross-sectional top views of the monitoring system shown in FIG. 8.
Figure 12:
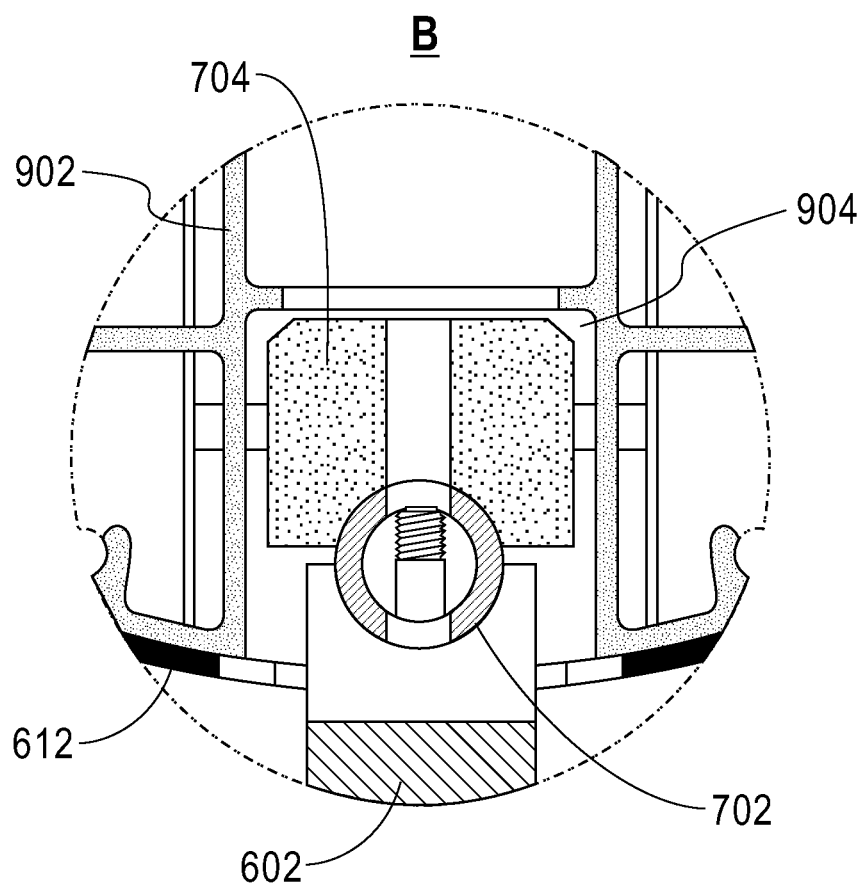

Referring now more specifically to FIGS. 8, 9, 10, 11, and 12, a more detailed discussion of the internal structure and arrangement of the Monitor System 100 is provided, according to various embodiments of the present disclosure. As shown in FIG. 8, the Monitor System 100 and its internal structure and construction will be further discussed with reference to two cut-away views. A first cut-away view, indicated by the arrows labeled 9 in FIG. 8, and shown in FIG. 9, shows a side view of the internal structure of the Monitor System 100. Additionally, a second cut-away view indicated in FIG. 8 by the arrows labeled 11, and shown in FIG. 11 and in more detailed in FIG. 12, shows a more detailed view of the internal backbone 902 inside the outer cover 612 of the vertical spine 106 and the mechanical support 602 of the OSR 104 within the vertical spine 106.

Referring to FIGS. 9 and 10, the side cut-away view highlights the backbone structure 902 that runs the length of the vertical spine 106 from the controller unit 112 down to the base 108. The backbone structure 902 includes an integrated impact channel 904 that runs a length of the backbone structure 902 as best viewed in FIGS. 9 and 10. The backbone 902 with the integrated impact channel 904 is a highly sensitive mechanical system that is resistant to damage.

The channel impactor block 704 is moveably held in the impact channel 904 such that the impactor block 704 can slide up and down along the inside of the impact channel 904. According to the present example, there is an air gap between the impactor block 704 and the walls of the impact channel 904. The air gap would also be between the pushrod 702 and the walls of the impact channel 904. The ring mount 602 is secured to the channel impactor block 704, such as with 2 bolts that secure the ring mount 602 to the channel impactor block 704. The ring mount 602 is also secured by these 2 bolts to the pushrod 702. The pushrod 702, by the ring mount 602, supports the OSR 104 on the load cell 706 in the base 108. A downward force imparted on the OSR 104 is transferred through the pushrod 702 to the load cell 706 in the base 108.

It should be noted that the air gap allows the pushrod 702 and the channel impactor block 704 to move vertically without friction from contact with the walls of the impact channel 904 while the pushrod 702 in the impact channel 904 is protected from impact by the walls of the impact channel 904.

Further, while the present example uses an air gap to separate the pushrod 702 and the channel impactor block 704 from the walls of the impact channel 904, other gases and fluids may be used to separate and allow vertical movement of the pushrod 702 and the channel impactor block 704 without friction from contact with the walls of the impact channel 904 and while the pushrod 702 in the impact channel 904 is protected from impact by the walls of the impact channel 904. For example, and not for limitation, the entire impact channel 904 may be enclosed, such as by a flexible film enclosure made from material such as silicone, to contain a suitable gas, other than air, or a suitable fluid, that allows vertical movement of the pushrod 702 and the channel impactor block 704 without friction from contact with the walls of the impact channel 904. The enclosing material, such as silicone film, is supported by the impact channel 904 and does not add any significant weight to the pushrod 702 during its operation. The pushrod 702 would move in the impact channel 904 without friction from contact with the walls of the impact channel 904 and while being protected from impact by the walls of the impact channel 904. As an example, and not for any limitation, a fluid such as a light machine oil with suitable viscosity can be contained in the impact channel 904 to allow the vertical movement of the pushrod 702 and the channel impactor block 704 without friction from contact with the walls of the impact channel 904. The enclosing material, such as the silicone film, and the fluid are supported by the impact channel 904 and do not add any significant weight to the pushrod 702 during its operation. The light machine oil with suitable viscosity would help cushion and protect the pushrod 702 from impact by the walls of the impact channel 904 while allowing the vertical movement without friction from contact with the walls of the impact channel 904. The fluid-filled impact channel 904 would provide a highly sensitive mechanical system allowing the vertical movement of the pushrod 702 without friction from the walls of the impact channel 904 while cushioning and protecting the pushrod 702 from impact with the walls of the impact channel 904, thereby being resistant to damage to the pushrod 702. Lastly, while the example discussed above uses a gas other than air, or a fluid, to entirely fill the impact channel 904, it should be noted that less than an entire length of the impact channel 904 may be filled. For example, a portion of the length of the impact channel 904 may be enclosed, such as by a flexible film enclosure made from material such as silicone, to contain a suitable gas, other than air, or a suitable fluid, that allows vertical movement of the pushrod 702 and the channel impactor block 704 without friction from contact with the walls of the impact channel 904. The enclosing material, such as silicone film, and the fluid contained in the enclosure when a fluid is used, are supported by the impact channel 904 and do not add any significant weight to the pushrod 702 during its operation. According to one embodiment of the present disclosure, the portion of the length of the impact channel 904 would contain both the pushrod 702 and the channel impactor block 704.

FIG. 10 shows an enlarged view labeled A of the mechanical coupling and support between the OSR 104, the ring mount 602, and the impactor block 704 held in the impact channel 904. When downward force is applied to the OSR 104 it transfers the downward force via the ring mount 602 to the pushrod 702. The impactor block 704 helps keep the OSR 104 substantially steady in a horizontal direction while the ring mount 602 transfers the downward force to the pushrod 702. The downward force on the OSR 104 is transferred to the pushrod 702 which delivers this downward force down to the load cell 706 in the base 108 of the Monitor System 100. In this way, the Monitor System 100 can very accurately sense the incremental weight of objects being deposited in the container 101 supported by the OSR 104.

With reference to FIGS. 11 and 12, the backbone structure 902, the impact channel 904, the impactor block 704, and the pushrod 702, are shown in more detail. The dashed-lined circle labeled B in FIG. 11 is shown in an enlarged view in FIG. 12. As can be seen, the ring mount 602 is bolted to the pushrod 702 and to the impactor block 704. The impactor block 704 is moveably secured within the impactor channel 904 of the backbone structure 902. The impactor block 704 helps keep the ring mount 602 substantially steady in a horizontal direction. The impactor block 704 secured to the pushrod 702 can both move in a vertical direction thereby transferring the downward force from the ring mount 602 to the pushrod 702 and thereby to the load cell 706.

Figure 13:
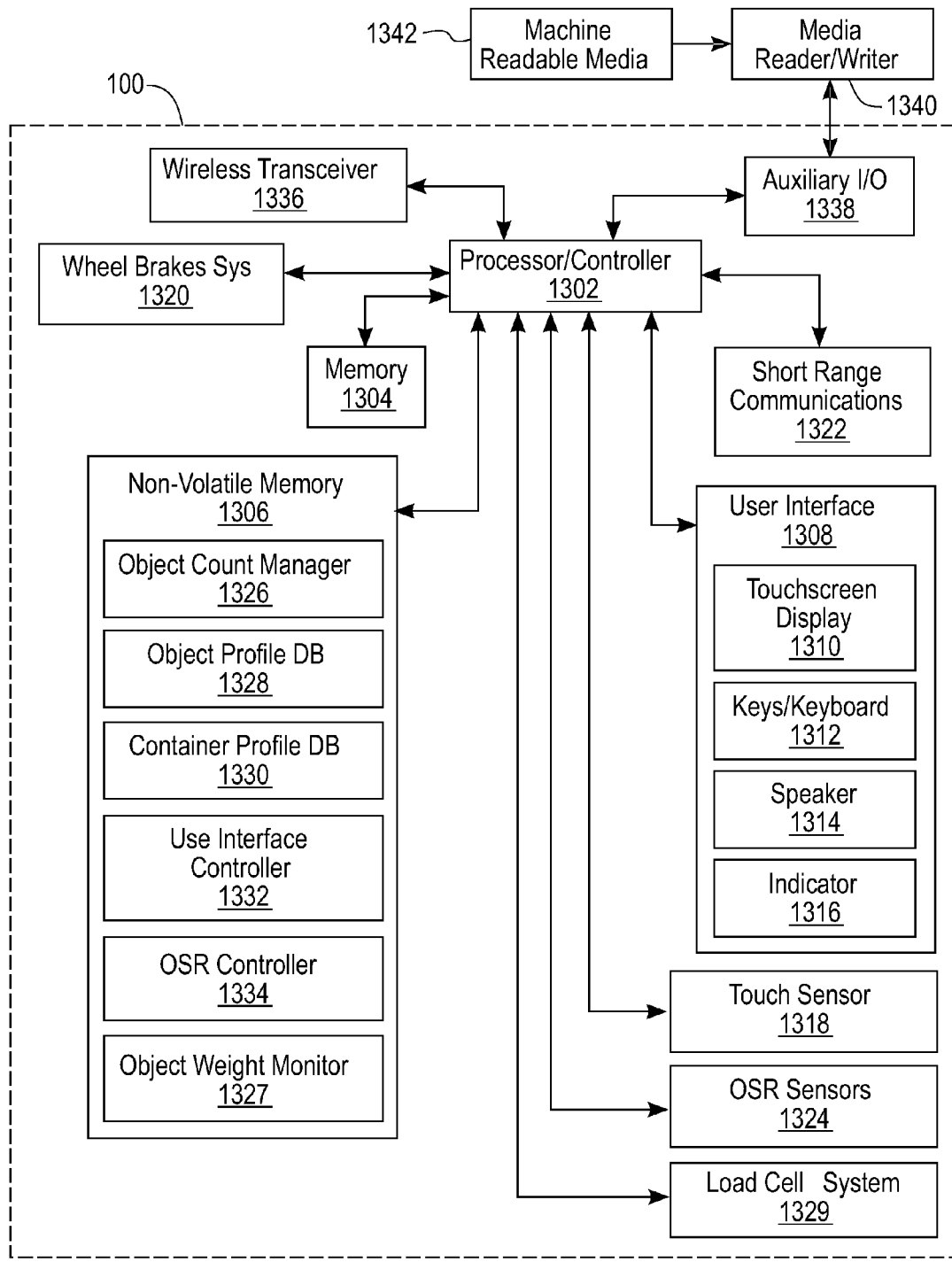
FIG. 13 is a functional block diagram of an example of a monitoring system, according to the present disclosure.

Referring to FIG. 13, a functional block diagram of an example of the Monitor System 100 is shown. This is only one example of a Monitor System 100, and many different variations are anticipated in connection with the present disclosure.

The Monitor System 100, according to the present example, includes a processor/controller 1302 communicatively coupled with memory 1304 and with non-volatile memory 1306. With reference to memory, according to the present disclosure, any one or a combination of non-volatile memory or volatile memory can be utilized according to the present disclosure in the particular context that the memory is used. The processor/controller 1302 interoperates with the memory 1304, 1306, to perform instructions stored in the memory 1304, 1306, and utilizing configuration parameters and other parameters stored in the memory 1304, 1306, thereby implementing the new and novel methods of the present disclosure. The non-volatile memory 1306 comprises persistent memory that stores computer instructions and data persistently even when electrical power is removed from the Monitor System 100.

A user interface 1308 is communicatively coupled with the processor/controller 1302. The user interface 1308 provides user input interface elements such as a touch screen display 1310 and keys/keyboard 1312 that allow a user of the Monitor System 100 to enter information, commands, and configure features and functions of the Monitor System 100. The user interface 1308 also includes user output elements such as the touch screen display 1310 which provides a display of information to the user, a speaker 1314 that provides audible signals to the user, and one or more indicators 1316 which provide various types of indicator signals to the user. The indicator 1316, for example, can include one or more LED indicators that provide visual information to the user, one or more audible indicators that provide audible signals to the user, or optionally a tactile indicator that provides tactile information (e.g., vibration signals) to the user. Any one or more of these user interface elements 1310, 1312, 1314, 1316 may be used by the processor/controller 1302 to communicate with the user of the Monitor System 100, according to various embodiments of the present disclosure.

The processor/controller 1302, according to the present example, is communicatively coupled with a touch sensor 1318 which senses when a user touches an outer surface of the Monitor System 100. For example, when the user's hand 208 grabs the handle 116 (see FIG. 2), the processor/controller, using the touch sensor 1318, detects this event. The touch sensor 1318, according to one example, may comprise a variable frequency circuit that responds to the capacitive influence of a user's hand 208 in close proximity or contact with an outer surface (e.g., the handle 116) of the Monitor System 100. In this way, the processor/controller 1302 can detect a user's contact with the outer surface of the Monitor System 100.

When the processor/controller 1302, for example, detects that the user is grabbing the handle 116, the processor/controller 1302 can control a wheel brake system 1320 to release brakes from the plurality of wheels 110. As an example, the processor/controller 1302 may electrically control one or more solenoids that control mechanical brakes at each of the wheels 110, respectively. The processor/controller 1302 causes the solenoids to switch and thereby release the brakes from the wheels 110 when the processor/controller 1302 determines that a signal from the touch sensor 1308 indicates that the user is grabbing the handle 116. This allows the user to easily roll and move the Monitor System 100 on the floor to a desired location. Alternatively, when the user's hand 208 is released from the handle 116, the processor/controller 1302 determines that a signal from the touch sensor 1308 indicates this event. The processor/controller 1302 then electronically controls one or more solenoids in the wheel brake system 1320 that cause the mechanical brakes to promptly engage with each of the wheels 110, respectively, and thereby immobilize the Monitor System 100 at the precise present location. It should be noted that while a wheel brake system 1320 is discussed, according to the present example, it may additionally (or alternatively) control a wheel motor system that when the one or more motors are disabled, it immobilizes the Monitor System 100. When the one or more motors are enabled by the processor/controller 1302, the wheels 110 can rotate thereby allowing the Monitor System 100 to be moved.

The processor/controller 1302 is communicatively coupled with short range communications circuitry 1322 that facilitate communications between the Monitor System 100 and other devices located in the near vicinity of the location of Monitor System 100. These other devices are similarly equipped with short range communications circuitry that allows them to receive communications from the Monitor System 100, send communications to the Monitor System 100, or both. These short range communications include wireless communications that do not require the device and Monitor System 100 to be tethered together.

According to various embodiments, the short range communications circuitry 1322 includes RFID communication circuitry 305, 307, that allows the processor/controller 1302 to communicate with similarly equipped RFID devices in the near vicinity of the Monitor System 100.

For example, the container 101, according to various embodiments, can include an RFID device. The RFID device, as an example, is embedded in the top 103 of the container 101. The RFID device in the container 101 may include one or more pieces of information that can be used by the Monitor System 100. For example, an identification code in the RFID device embedded in the top 103 of the container 101 can be transmitted, in response to interrogation signals transmitted over short range communications by the processor/controller 1302 utilizing the short range communications circuits 1322 (also, for example, see the first 305 and second 307 RFID communication circuitries shown in FIG. 3) in the Monitor System 100. This identification code of the container 101 may identify a container profile to the Monitor System 100 thereby allowing the Monitor System 100 to: (1) identify that a container 101 is in close proximity and/or mounted on the OSR 104, and (2) uniquely identify the type of container 101 that is being used by the Monitor System 100. The type of container may additionally indicate the number of openings 206 in the top 103 of the container 101, and the specific locations of the one or more openings 206. The RFID device on the container can also double up, and be used, to replace a wireless switch (e.g. IR switch) or a wired mechanical switch [normally housed on the outside of the Optical Sensor Ring (OSR)] to inform the processor/controller 1302 when a container is securely placed on the OSR or taken off the OSR by a user.

These short range communications between the Monitor System 100 and the container 101 being used by the Monitor System 100 can make it easy and fool proof for a user to use a container 101 mounted on the OSR 104 of the Monitor System 100. For example, the user can take the container 101 out of its protective packaging and while holding the top 103 by its handles lowers the opened and fully formed container into the ring center opening of the OSR 104 thereby mounting the container 101 on the OSR 104. The processor/controller 1302, using the short range communication circuits 1322 wirelessly interrogates the RFID device in the container 101. The processor/controller 1302 thereby determines the container's profile information, which may be stored in memory such as in a container profile data base 1330.

The Monitor System 100 will then be ready to be used by the user according to default settings configured in the non-volatile memory 1306. The processor/controller 1302, based on the information in the container profile data base 1330, determines the locations of the one or more openings 206 in the top 103 of the container 101 that is mounted on the OSR 104.

The processor/controller 1302, according to various embodiments, controls OSR sensors 1324 located on the inner ring surface 606 of the OSR 104. The OSR sensors 1324 include one or more optical transmitters matched with optical sensors that create one or more optical beams traversing across the ring center opening of the OSR 104. For example, an optical emitter on the inner ring surface 606 at one of the back portions 608 or front portion 610 is matched with an opposing optical sensor on the inner surface 606 of the other one of the back portions 608 and the front portion 610 of the OSR 104. Utilizing the OSR sensors 1324, the processor/controller 1302 can detect when one or more of the optical beams break due to an object entering one of the one or more openings 206. The object blocks (i.e., "breaks") the optical beam emitted from the optical emitter from reaching the matching optical sensor on the opposite inner surface 606 of the OSR 104.

An object count monitor 1326 is stored in the non-volatile memory 1306 and interoperates with the processor/controller 1302 to count objects 204 that are placed in the one or more openings 206 of the top 103 of the container 101. As the object 204 enters one of the one or more openings 206, according to the present example, the one or more OSR sensors 1324 detect the "beam break" event and communicate one or more beam break signal(s) to the processor/controller 1302. The object count monitor 1326 can then determine whether a valid object has been detected, as will be discussed below.

It should be noted that in certain embodiments, one or more RFID communication circuitries 305, 307 (e.g., at least one RFID reader) in the Monitor System 100 are located, for example, and not for any limitation, at or about the one or more openings 206, such as at about or in the OSR 104. The one or more RFID communication circuitries 305, 307 may be located at one or more suitable locations in the Monitor System 100. In this arrangement, according to the present example, objects 204 including at least one RFID device 205 can be monitored/interrogated (e.g., via the information in the object's respective RFID device 205) entering the one or more openings 206 at the top 103 of the container 101 (e.g., monitored by the one or more RFID communication circuitries 305, 307). Moreover, as has been discussed above with reference to FIG. 3, objects 204 can be further monitored to be placed inside the container 101 at one or more levels vertically along the container 101 from the top 103 of the container 101 along the container main body 102 to the bottom of the container 101.

The one or more RFID communication circuitries 305, 307, at or about the one or more openings 206 can provide a detection region just at or immediately below the one or more openings 206 to detect an object 204 including at least one RFID device 205 being placed into the one or more openings 206. Objects, such as sponges, 204 that include RFID devices 205, when in proximity to the at least one RFID reader 305, 307, can be quickly interrogated by the at least one RFID reader 305, 307, and thereby information associated with each such object and its RFID device 205, and including the approximate location of the particular object 204, can be determined by the Monitor System 100. As the object 204 enters one of the one or more openings 206, according to the present example, the one or more RFID communication circuitries 305, 307 detect the event of the object 204 entering the one or more openings 206 and communicate the information, including the event detection signal, to the processor/controller 1302. The object count monitor 1326 can then confirm whether a valid object has been detected entering the container 101, as will be discussed below.

Furthermore, it should be noted that object profile information associated with each object 204 and its RFID device(s) 205 to be used in a procedure (e.g., a surgical procedure) can be pre-stored in memory, e.g., in an object profile database 1328, of the Monitor System 101, prior to the object's use during the surgical procedure. Such information may include, for example but not limited to, RFID codes associated with individual RFID device(s) included with the object, universal address information uniquely identifying each individual RFID device, group address information that uniquely identifies each individual RFID device as being associated with a group of RFID devices to be used in a particular surgical procedure (or in another particular use of the group of RFID devices), and other object profile information such as object attributes, RFID device attributes, and other related information that can be tracked for each object and its one or more RFID devices.

According to various example system configuration procedures, object profile information associated with each object (e.g., with each sponge) and its RFID device(s) 205 can be collected and stored in the Monitor System 101, such as in the object profile database 1328, using different ways of entering information into the object profile database 1328. As one example system configuration procedure, the processor/controller 1302 can communicate with an external computing device via a communication interface such as the auxiliary I/O interface 1338 to receive a collection of object profile information that can be stored into the object profile database 1328 for each object and its one or more RFID devices. As a second example system configuration procedure, during a configuration procedure the profile information from one or more objects (e.g., sponges) and including their RFID device(s) identification and other related information can be entered into the object profile database 1328 by a technician user of the Monitor System 101. The user can manually enter such object profile information for each object and its included RFID device(s) by using the user interface 114. As a third example system configuration procedure, the Monitor System 101 during a configuration procedure can automatically interrogate and wirelessly receive and collect the object profile information from one or more objects (e.g., sponges) located in the vicinity of the short range communication circuits 1322. This collected object profile information for each such object (e.g., each sponge) and its RFID device(s) can be stored by the processor/controller 1302 in the object profile database 1328. In this third example, the processor/controller 1302 uses an RFID device discovery procedure using a wireless communication protocol between the processor/controller 1302 (communicating via the short range communication circuits 1322) and the one or more objects (e.g., sponges) including their RFID device(s), to detect the RFID device(s) for each object (e.g., sponge). The processor/controller 1302 then wirelessly interrogates, wirelessly receives, captures, and collects from the RFID device(s) the object profile information and stores the information in the object profile database 1328. According to certain embodiments, the processor/controller 1302 may additionally configure the RFID device(s) to include certain information associated with the Monitor System 101 and optionally with the particular surgical procedure (or other procedure) in which the objects and their RFID device(s) will be used. For example, in addition to storing for each object and its RFID device(s) certain group address information in the object profile database 1328, the processor/controller 1302 may additionally wirelessly communicate with and configure (e.g., cause the store of codes and information in) each RFID device with the group address information to uniquely identify each individual RFID device as being associated with a group of RFID devices to be used in a particular surgical procedure (or in another particular use of the group of RFID devices).

Detection of an object 204 entering an opening 206 at the top 103 of the container 101, as has been discussed above, may be accomplished in one or more ways. According to one alternative, one or more OSR sensors 1324, for example, can detect a "beam break" event and communicate one or more beam break signal(s) to the processor/controller 1302. The object count monitor 1326 can then determine whether a valid object has been detected entering the opening 206. According to a second alternative, one or more RFID communication circuitries 305, 307, at or about the one or more openings 206 can detect an object 204 including at least one RFID device 205 being placed into the one or more openings 206. Objects, such as sponges, 204 that include RFID devices 205, when in proximity to the at least one RFID reader 305, 307, can be quickly interrogated by the at least one RFID reader 305, 307, and thereby information associated with each such object and its RFID device 205, and including the approximate location of the particular object 204, can be determined by the processor/controller 1302. The object count monitor 1326 can then confirm whether a valid object has been detected entering the container 101. As a third alternative, a combination of the first alternative and the second alternative discussed above may be implemented. That is, both the one or more OSR sensors 1324 can detect a "beam break" event and communicate one or more beam break signal(s) to the processor/controller 1302 and contemporaneously the one or more RFID communication circuitries 305, 307, at or about the one or more openings 206 can detect an object 204 including at least one RFID device 205 being placed into the one or more openings 206 and communicate the information to the processor/controller 1302. This combination detection of an object 204 being placed in the one or more openings 206 provides an enhanced level of detection reliability to detect the object 204 entering the opening 206 and additionally obtaining information from the object 204 (from its at least one RFID device 205) to more reliably identify the object 204 entering the opening 206. Furthermore, a single opening 206 in a container 101 may be used to reliably detect (and identify) objects 204 entering the container 101 via the opening 206.

According to the present example, an object profile data base 1328 is stored in the non-volatile memory 1306. This object profile data base 1328 keeps track of certain attributes and characteristics of objects that may be monitored in certain applications of the Monitor System 100. For example, a certain size of sponge entering an opening 206 of the container 101 may be detected and identified using the object profile data base 1328. Besides the size of the sponge, the object profile data base 1328 may identify the typical "dry" weight of the object being dropped into the one of the openings 206. Other characteristics of the object may likewise be stored in the object profile data base 1328. For example, a maximum fluid filled weight for the particular object identified in the object profile data base 1328 may also be stored in the data base 1328. This allows the Monitor System 100 to determine a valid range of weight of the particular object detected entering the particular opening 206.

A user interface controller 1332 is stored in the non-volatile memory 1036. The user interface controller 1332 interoperates with the processor/controller 1302 to control elements 1310, 1312, 1314, 1316 of the user interface 1308. An OSR controller 1334 interoperates with the processor/controller 1302 to control and monitor the OSR sensors 1324.

A wireless transceiver 1336 is communicatively coupled with the processor/controller 1302. The processor/controller 1302 can utilize the wireless transceiver 1336 to wirelessly communicate with other devices and/or systems. For example, other monitoring systems in a surgical operating room (surgical OR) may be communicating information with the Monitor System 100.

For example, a separate fluid monitoring system may be wirelessly coupled via the wireless transceiver 1336 with the Monitor System 100 and thereby provide fluid loss information to the Monitor System 100, such as during a surgical procedure. The Monitor System 100, according to the present example, can aggregate fluid loss data from the other system (or systems) in wireless communication with the Monitor System 100. As a non-limiting example, a separate fluid loss monitoring system can continuously collect fluid loss data with respect to urine and fluids in the wall suction during a surgical procedure; which such fluid would be weighed by the separate system and the weight converted to a fluid volume estimate. The other separate fluid loss monitoring system, being communicatively coupled via established communications (wireline or wireless) with the Monitor System 100, transmits periodically or in response to query (or queries) from the Monitor System 100, its collected fluid loss data to the Monitor System 100. The fluid loss data from the one or more other system(s) can be combined by the Monitor System 100 with fluid loss information directly collected by the Monitor System 100 from the patient during a surgical procedure (e.g., by calculating estimated fluid loss of the patient from fluid-filled sponges being deposited into the container 101 supported by the OSR 104 in connection with the surgical procedure). In this way, the Monitor System 100, according one embodiment, could operate as a "command center" for monitoring overall fluid loss from a patient. The Monitor System 100 can provide via the user interface 1308 aggregated fluid loss information to the medical doctor, nurse, nurse anesthetist, and the scrub technician, or any user.

An object weight monitor 1327 stored in the non-volatile memory 1306 interoperates with the processor/controller 1302 to determine the weight of each object being dropped into the container 101. The object weight monitor 1327 uses electrical signals received by the processor/controller 1302 from the load cell system 1329 to determine the weight of the object. The object weight monitor 1327 can determine the object's weight and additionally can determine the amount of fluid contained in the object.

For example, the object profile data base 1328 would include the typical "dry" weight of the particular object, i.e., without carrying fluid in the object. The object weight monitor 1327 can subtract the typical "dry" weight of the object from the measured weight of the object detected in the container 101 thereby calculating a weight of fluid carried in the object dropped in the container 101.

The load cell system 1329 comprises an electronic load cell 706 that detects the downward force applied from the pushrod 702 that is mechanically coupled via the ring mount 602 to the OSR 104 supporting the container 101. This downward force on the electronic load cell 706 comprises the weight of the object being placed in the container 101 that is supported by the OSR 104. The load cell system 1329 provides an electrical signal (corresponding to the weight of the object) to the processor/controller 1302. In this way, the processor/controller 1302 determines the weight of the object that is deposited in the container 101.

Auxiliary input-output circuitry 1338 is communicatively coupled with the processor/controller 1302 and allows the processor/controller to communicate with an external media reader/writer 1340. The media reader/writer 1340 can receive machine readable media 1342 and provide the instructions and/or data stored in the machine readable media to the processor/controller 1302 via the auxiliary input-output circuits 1338. In this way, the processor/controller 1302 can receive instructions and data for performing the novel features and functions according to the present disclosure.

In addition to loading applications software and/or configuration parameters into the Monitor System 100 as part of a manufacturing process, applications and/or configuration parameters can be loaded into the Monitor System 100 through, for example, a wireless network in communication with the wireless transceiver 1336, an auxiliary I/O device 1338, a USB port (not shown), a short-range communication subsystem 1322, or any combination of these interfaces. Once these software applications are loaded into the Monitor System 100, these applications are executable with the processor/controller 1302.

A media reader/writer 1340 is able to be connected to the auxiliary I/O device 1338 to allow, for example, loading computer readable program code of a computer program product into the Monitor System 100 for storage into, for example, the non-volatile memory 1306. One example of a media reader 1340 is an optical drive such as a CD/DVD drive, which may be used to store data to and read data from a computer readable medium or computer storage product comprising computer readable storage media 1342. Examples of suitable computer readable storage media include optical storage media such as a CD or DVD, magnetic media, or any other suitable data storage device. The media reader 1340 is alternatively able to be connected to the Monitor System 100 through a USB port or computer readable program code is alternatively able to be provided to the Monitor System 100 through the wireless transceiver 1336.

Figure 14:
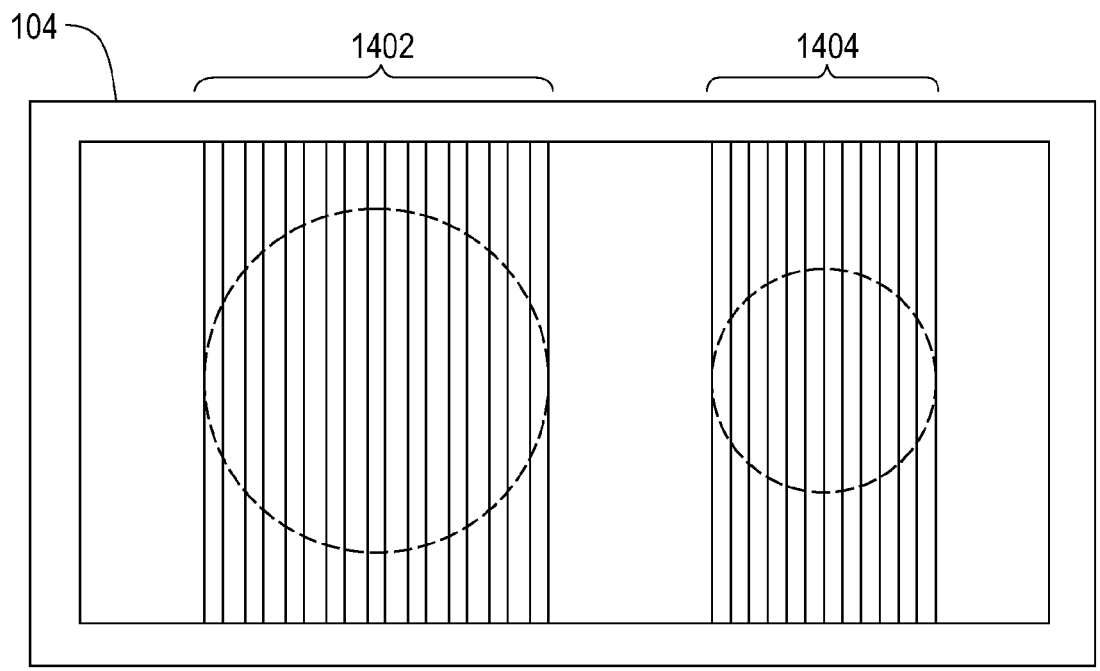
FIG. 14 is a planar top view of an optical sensor ring with two openings of a container located in a center opening of the optical sensor ring, according to the present disclosure.

FIG. 14 illustrates the OSR 104 during operation of the OSR sensors 1324, according to one example of the present disclosure. A first plurality of optical beams, e.g., infrared beams, 1402 traverse across the ring center opening of the OSR 104 covering a detection region just below the one or more openings 206 in the top 103 of a container 101. In FIG. 14, these openings 206 are represented by dashed-line circles.

The container 101 may be identified by the Monitor System 100 by information entered by: 1) a user 502 using the touchscreen display 114 (see FIG. 5), or 2) optionally in certain embodiments the container 101 may be identified by the Monitor System 100 using wireless communication to interrogate an RFID device located in the container 101, or 3) by a combination of both methods. With the container 101 being identified to the Monitor System 100, the Monitor system 100 can look-up the container profile information from the container profile data base 1330 and thereby determine the approximate location of the one or more openings 206 at the top 103 of the container 101.

While there can be OSR sensors 1324 along the entire inner surface 606 of the OSR 104, such as along the back portion 608 and the front portion 610 of the ring 104, (optionally also along the entire inner surface 606 of the left portion and the right portion of the OSR 104), the processor/controller 1302 during operation would activate only those beams 1402, 1404, (optionally at an appropriate time, also only those beams between the left portion and the right portion of the OSR 104), that cover the specific dimensions of the openings 206 of the top 103 of the particular container 101 identified in the container profile data base 1330. This is only one non-limiting example of using the OSR sensors 1324 according to the present disclosure.

There are many different ways to use optical sensors located along the inner surface 606 of the OSR 104 to detect objects placed in the one or more openings 206, which may include using one or more emitters/sensors along the rear portion matched with one or more sensors/emitters along the front portion of the OSR 104, or using one or more emitters/sensors along the left portion matched with one or more sensors/emitters along the right portion of the OSR 104, or any combination of both types of arrangements of sensors.

For example, a single plurality of optical beams across the entire inner surface 606 between the back portion 608 and the front portion 610 of the ring 104 may be activated and energized during a monitoring operation and only the beams 1402, 1404 covering the openings 206 may be broken, thereby indicating which opening an object was dropped in. This may be useful in an application where the type of container 101 and location of the openings 206 is not necessarily known by the Monitor System 100.

Optionally, a plurality of optical beams, between the inner surface of the rear portion of the OSR 104 and the inner surface of the front portion of the OSR 104, can be spaced apart a known distance from each other in the detection region below each opening 206. After at least one beam break is detected the sensors and the processor/controller 1302 can continuously monitor the beam break(s) while the object continues to fall past the detection region. The beam-break-sense monitoring, for example, can be repeated every 10 milliseconds until all of the optical beams are sensed again (i.e., no beam breaks detected).

It should be noted that the processor/controller 1302, according to the present example, would monitor the falling object for a maximum amount of fall time through the detection region. If at least one beam break is continuously sensed from the time a first beam break is sensed past the maximum amount of time allowed for an expected object to fall through the detection region, then the processor/controller would flag this as an error condition, and no object detection would be registered. This would be the case, for example, if an object (or possibly a user's hand) was placed at an opening 206 but no object falls into the container 101.

Figure 15:
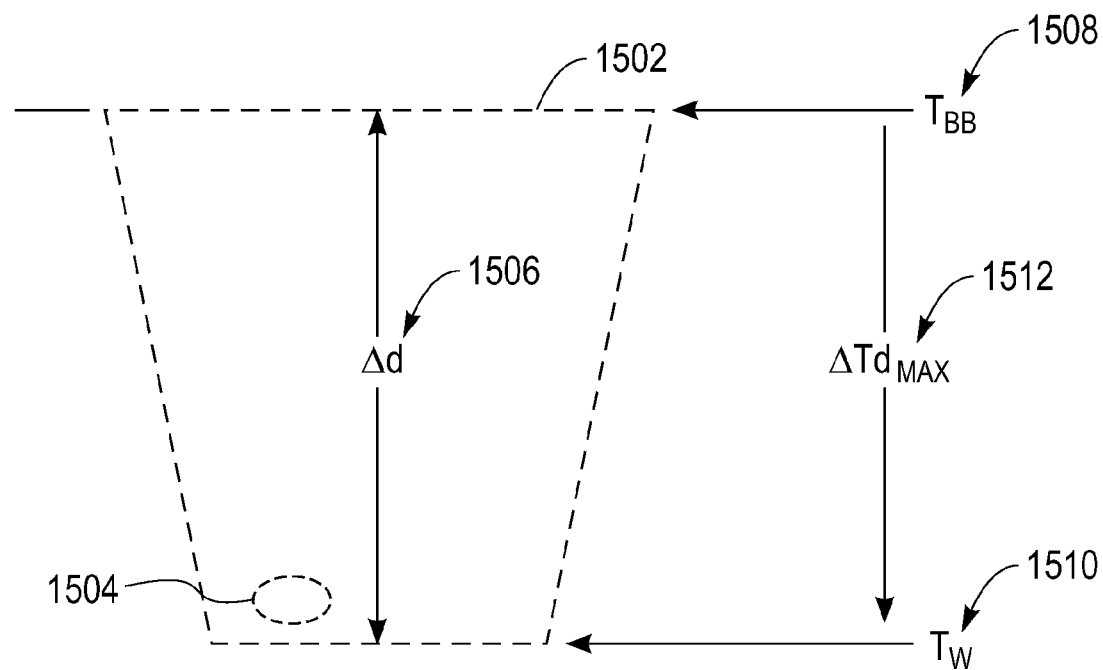
FIG. 15 is a planar side view of a container with an object contained in the container.

With reference to FIGS. 15 and 16, a description of one example of a method for detecting a valid object count and weight for the object will be discussed below. As shown in FIG. 15, a container 1502 is shown by the dashed lines 1502 with an object 1504 having been dropped into a compartment in the container 1502. The height of the container from the top 103 where the beam is broken (and/or where the one or more RFID communication circuitries 305, 307, at or about the one or more openings 206 detect an object 204 including at least one RFID device 205) to the bottom of the container which is the maximum drop distance is indicated by the symbol $\Delta_d$ 1506.

At a point in time labeled $T_{BB}$ 1508, the beam break is detected (and/or the RFID device 205 is detected in the detection region) and at a point in time $T_w$ 1510 is the time when weight is measured for the object 1504 having been dropped in the container 101, as indicated by the dashed line 1502. The maximum amount of time for a drop of the object 1504 is indicated by the symbol $\Delta T_{d\ max}$ 1512.

Referring now to FIG. 16, the graph shows the container 1502, 101 weight measurement starting at the left side of the graph with a recent baseline weight 1606. At a point in time $T_{BB}$ 1508 the beam break event is detected (and/or the RFID device 205 proximity detection event is detected) and the Monitor System 100 waits until a maximum amount of time for object drop (Delta $T_{d\ max}$) 1512 plus a Delta $T_s$ 1604 (i.e., noise signal settling time). This is the total amount of time Delta $T_w$ 1606 for taking a weight measurement at a point in time $T_w$ 1510.

As can be seen by the weight curve starting from the recent baseline weight 1606 up to the new weight 1608 there is a point in time when the object dropped hits the container 101 imparting a weight force on the container 1502, 101 and creating potential noise signal due to the vibrations of the object landing in the container 101, e.g., landing on the bottom of the container 1502, 101.

This settling time Delta $T_s$ 1604 is used as a delay to reduce the possibility that an improper weight signal will be measured during the noise signal portion from the load cell. The total amount of time delay Delta $T_w$ 1606 until the weight measurement is taken at a point $T_w$ 1510 assures that the weight measurement will be accurately measuring the new weight 1608 in the container 101 (without influence from any vibration noise signal). The Monitor System 100 captures the incremental weight 1610 which is the difference between the baseline weight 1606 and the new weight measurement 1608. This incremental weight Delta$_w$ 1610 indicates the weight of the object dropped in the container 1502, 101.

While the Monitor System 100 may capture and collect the absolute weight 1606, 1608, of the container 1502, 101 including the weight of the newly added object 1504, the incremental weight Delta$_w$ 1610 is directly indicative of the weight of the new object 1504 being deposited in the container 1502, 101. In this way, the Monitor System 100 can monitor the short term incremental weight Delta$_w$ 1610 following a beam break 1508 to indicate the weight of a new object having been dropped in the container 1502, 101.

This avoids also the absolute weight measurement 1606, 1608, possibly varying and creating a false positive under other circumstances. That is, for example, if an object is placed on the top 103 of the container 1502, 101, and not into the opening 206 of the container 101, it will not be detected as an incremental weight 1610 and the Monitor System 100 thereby avoids false positive detection. It should be noted that the absolute weight can vary without providing misinformation or false information to the Monitor System 100. The Monitor System 100, according to various embodiments, monitors the short term incremental weight Delta$_w$ 1610 from the point where the beam breaks $T_{BB}$ 1508. This provides a more accurate way of detecting that an object 1504 was dropped in the container 1502, 101, and the incremental weight Delta$_w$ 1610 of the object having been dropped in the container 1502, 101.

Figure 17:
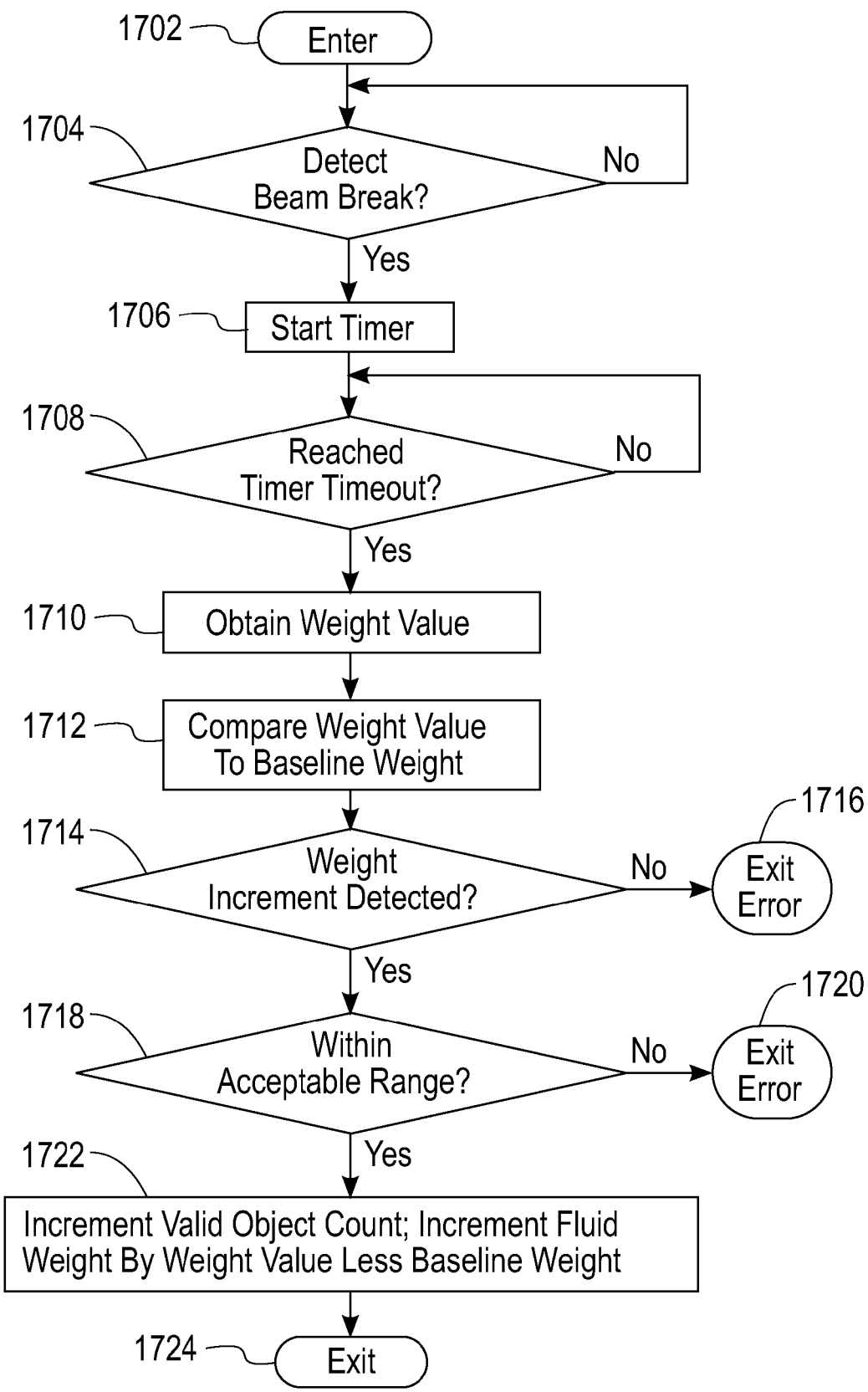
FIG. 17 is an operational flow diagram illustrating an example of an operational sequence performed with a monitoring system, according to the present disclosure.
Figure 18:
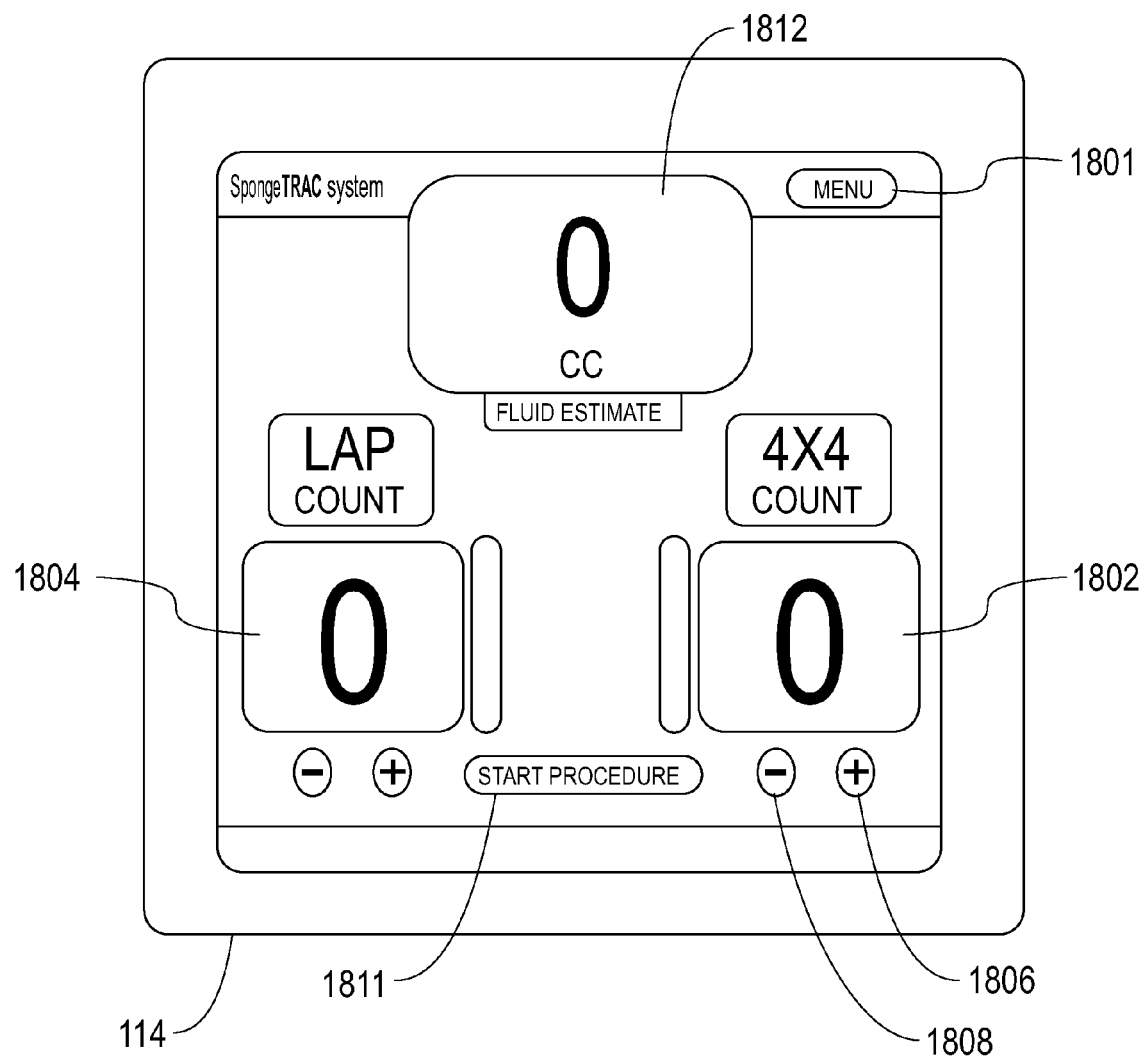
FIG. 18 is a planar front view of a touchscreen display for use with a monitoring system, according to the present disclosure.

With reference to FIGS. 17 and 18, the following discussion will illustrate an example operational sequence (shown in FIG. 17) for the Monitor System 100 of FIG. 1. Additionally, one example of a touchscreen display 114 (shown in FIG. 18) will be used with the Monitor System 100, according various embodiments of the present disclosure. A user of the Monitor System 100 can touch, for example, virtual buttons on the touchscreen display 114 to enter data, configure parameters, and invoke functions and features of the Monitor System 100, and the like. A virtual button 1801 labeled "menu" is located at the upper right region of the touchscreen display 114. The menu button 1801 allows the user to select various modes of user interaction with the user interface touchscreen display 114.

As one example of operation of the touchscreen display 114, as illustrated in FIG. 18, the touchscreen display 114 shows user interface elements corresponding to a container 101 with two openings 206. Each opening corresponds to known dimensions of a sponge being sorted and counted using the Monitor System 100. According to the present example, the right-side-count display 1802 is associated with the 4×4 sponge count while the left-side-count display 1804 is associated with the LAP sponge count.

These two counts 1802, 1804, correspond to the two respective openings 206 on the top 103 of the container 101. The right-side opening 206 is associated with the 4×4 sponge compartment in the container 101. The left-side opening 206 is associated with the LAP sponge compartment in the container 101. These are two separate compartments in the container 101.

By placing 4×4 sponges in the right-side opening 206, the right-side-count display 1802 changes to indicate the incremental count of sponges being deposited in the 4×4 sponge compartment in the container 101. Similarly, by placing LAP sponges in the left-side opening 206, the left-side-count display 1804 changes to indicate the incremental count of sponges being deposited in the LAP sponge compartment in the container 101. The incremental counts 1802, 1804, can be displayed counting up from zero to a total sponge count number, or alternatively can be displayed counting down to zero from a total sponge count number, as may be configured in the Monitor System 100 for the particular application. The right-side-count display 1802 is visually associated on the touchscreen display 114 with an up-count button 1806 and a down-count button 1808. These buttons 1806, 1808 allow the user to increase the number or decrease the number displayed in the right-side-count display 1802. A similar pair of buttons are visually associated with the left-side-count display 1804, as shown in FIG. 18. A fluid estimate value display 1812 shows the estimated amount of fluid being carried with the sponges that are deposited through the two openings 206 and into the container 101. This fluid estimate value 1812 displayed to the user can indicate an estimated amount of fluid loss of a patient during a surgical procedure.

To begin an operational sequence that uses the object counting and fluid estimation features of the Monitor System 100, the user can press the button labeled "start procedure". The Monitor System 100 will be activated to start monitoring for objects being placed in the openings 206.

FIG. 17 will now be referenced to illustrate an example operational sequence using the Monitor System 100. The processor/controller 1302 (see FIG. 13) enters the operational sequence, at step 1302, and proceeds to monitor, at step 704, the OSR sensors 1324 to detect whether an optical beam has been broken by an object being placed at one of the openings 206. While all optical beams remain unbroken, the processor/controller 1302 continues monitoring, at step 1704.

When an optical beam is detected broken, at step 1704, the processor/controller 1302 starts a timer, at step 1706, that counts the maximum amount of time 1512 allowed for an object to drop into the container 1502, 101, plus a maximum settling time 1604. The sum of both maximum time values 1512, 1604, defines a total time delay 1606 for then taking a weight measurement from the load cell system 1329. The maximum amount of time 1606 is monitored by counting with the timer, at step 1708. When the timer reaches the timeout time, at step 1708, the processor/controller 1302 obtains a weight value (i.e., a weight force value, also referred to as a weight force, sensed by the load cell system), at step 1710, from the load cell system 1329. This is also indicated in FIG. 16 at the point in time labeled $T_w$ 1510.

The processor/controller 1302, at step 1712, compares the new weight measured with the load cell system 1329 to the baseline weight previously measured (just before the beam break event was detected). Note that while the processor/controller 1302 remains waiting for detection of a beam break, at step 1704, it continuously samples new weight measurements (i.e., new weight force values, also referred to as a new weight force, sensed by the load cell system) from the load cell system 1329, and saves each measurement in order to determine the most recent baseline weight value for the container 101 upon a beam break event. Thus, since the incremental weight of an object that breaks the beam is determined relative to the most recent baseline weight value of the container, it is not necessary to determine the absolute weight of the container. Hence, unlike an accurate weigh-scale, this load-cell system 1329 does not necessitate on-going calibration, maintenance or set-up to ensure absolute weight measurement. Additionally, if a foreign weight (e.g. tray, tongs, etc.) is placed on the container, then this temporary or permanent addition to the overall container weight sensed by the load-cell system 1329 will not affect the determination of a true incremental weight (i.e. relative change in weight) arising from an object thrown into the container. Additionally, the fluid content of the object extracted/calculated from its incremental weight is used to accumulate the total fluid weight, hence, any extraneous weight placed on the container (or removed via evaporation of fluid) would not factor into the accumulated total fluid weight.

If a weight increment is detected, at step 1714, then the processor/controller 1302 continues to determine, at step 1718, whether the incremental weight of the new object in the container 101 is within acceptable range (within a tolerance limit). However, if a new weight increment is not detected, at step 1714, then the operational sequence exits with error, at step 1716. This may be the case where the optical beam is broken, such as by a user's hand or object being placed at the opening 206 but no object is dropped into the container 1502, 101.

With a measured weight increment being detected, at step 1714, the incremental weight of the object is compared to an acceptable range of weight for the object, at step 1718. If the weight of the object is not within an acceptable range (a tolerance limit), at step 1718, the operational sequence then exits with error at step 1720. This may be the case where an improper object has been dropped into the container 1502, 101.

If the incremental weight of the object dropped into the container 101 is within acceptable range, at step 1718, then the processor/controller 1302 determines that it is a valid object. The processor/controller 1302 then increments, at step 1722, a valid object count for the particular opening 206 at the top 103 of the container 1502, 101. That is, either the right-side-count display 1802 or the left-side-count display 1804 is incremented, as shown in FIG. 18. The incremental counts 1802, 1804, can be displayed counting up from zero to a total sponge count number, or alternatively can be displayed counting down to zero from a total sponge count number, as may be configured in the Monitor System 100 for the particular application.

Additionally, the processor/controller 1302 increments a total fluid weight value, at step 1722, by the incremental fluid weight value for the object placed in the container 1502, 101. The incremental fluid weight would be determined by at least taking the new weight value 1608 and subtracting from it the baseline weight value 1606 being tracked by the processor/controller 1302 and comparing the difference weight value (i.e., the total weight of the object, including any fluid contained therein) to an expected weight value for a "dry" (non-fluid filled) object such as a non-fluid filled sponge. The incremental weight value above the expected "dry" weight value would be attributable to fluid weight, at step 1722. This update to the total fluid weight value, at step 1722, can be displayed as a fluid estimate by volume in the fluid estimate volume display 1812. The fluid estimate value display 1812 shows the estimated amount of fluid being carried within the sponges that are deposited through the two openings 206 and into the container 101. This fluid estimate value 1812 displayed to the user can indicate an estimated volume of fluid in ml or cc absorbed/accumulated/collected in sponges during an operative procedure. The operational sequence then exits, at step 1724.

The present subject matter can be realized in hardware, software, or a combination of hardware and software. A system can be realized in a centralized fashion in one computer system, or in a distributed fashion where different elements are spread across several interconnected computer systems. Any kind of computer system—or other apparatus adapted for carrying out the methods described herein—is suitable.

The present subject matter can also be embedded in a computer program product, which comprises all the features enabling the implementation of the methods described herein, and which—when loaded in a computer system—is able to carry out these methods. Computer program in the present context means any expression, in any language, code or notation, of a set of instructions intended to cause a system having an information processing capability to perform a particular function either directly or after either or both of the following a) conversion to another language, code or, notation; and b) reproduction in a different material form.

Each computer system may include, inter alia, one or more computers and at least a computer readable medium allowing a computer to read data, instructions, messages or message packets, and other computer readable information from the computer readable medium. The computer readable medium may include computer readable storage medium embodying non-volatile memory, such as read-only memory (ROM), flash memory, disk drive memory, CD-ROM, and other permanent storage. Additionally, a computer medium may include volatile storage such as RAM, buffers, cache memory, and network circuits. Furthermore, in certain embodiments of the computer readable medium other than a computer readable storage medium as discussed above, the computer readable medium may comprise computer readable information in a transitory state medium such as a network link and/or a network interface, including a wired network or a wireless network, that allow a computer to read such computer readable information.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A surgical object and fluid monitoring system, comprising:
   a support ring for securely supporting a container with at least one port opening of the container being disposed for receiving surgical objects placed into the container through the at least one port opening with the aid of gravity;

a hollow spine structure vertically oriented and comprising a channel with channel walls along the length of the hollow spine structure;

a rod movably disposed in the channel within the hollow spine structure, the rod moveable along the channel;

a weight force sensing device mechanically coupled to the rod, the support ring mechanically coupled to the rod, and the rod being in a moving arrangement that transfers weight force from the support ring to the weight force sensing device;

a flexure mechanically coupled with the rod and the hollow spine structure, the flexure adding very little if any downward force onto the rod and thereby onto the weight force sensing device while maintaining the rod vertically aligned in the channel with a gap separating the length of the rod from the channel walls, the gap allowing the rod to move vertically without friction from contact with the channel walls while the rod in the channel is protected from impact by the channel walls; and a processor communicatively coupled with the weight force sensing device, wherein the processor, responsive to executing computer instructions, performs operations comprising:

detecting, with one or more RFID communication circuitries communicatively coupled with the processor, placement of a surgical object including at least one RFID device into the container through one of the at least one port opening with the aid of gravity by the one or more RFID communication circuitries interrogating the at least one RFID device of the surgical object being placed into the container;

determining an incremental weight of the contents of the container from the surgical object placed into the container through the port opening, based at least on an information signal received from the weight force sensing device indicating a change in weight force sensed by the weight force sensing device contemporaneous with the placement of the surgical object into the container through the at least one port opening with the aid of gravity.

2. The system of claim 1, further comprising:

one or more RFID communication circuitries communicatively coupled with the processor, arranged proximate to the support ring and to at least one port opening of a container that is supported by the support ring; and wherein the processor, responsive to executing computer instructions, performs operations comprising:

detecting placement of a surgical object into the container through the at least one port opening by monitoring at least one RFID device of the surgical object being located in a detection region proximate to the one or more RFID communication circuitries; and contemporaneous with the detecting, receiving the information signal from the weight force sensing device.

3. The system of claim 2, wherein the one or more RFID communication circuitries comprise a first RFID communication circuitry located at a back portion of the support ring and a second RFID communication circuitry located at a front portion of the support ring.

4. The system of claim 2, further comprising:

a plurality of pairs of emitter matched to sensor devices, arranged about the support ring to blanket the at least one port opening with one or more beams from the plurality of pairs; and wherein the processor, responsive to executing computer instructions, performs operations comprising:

detecting placement of a surgical object into the container through the at least one port opening by monitoring at least one of:

at least a break in one of the one or more beams that blanket the at least one port opening; and at least one RFID device of the surgical object being located in a detection region proximate to the one or more RFID communication circuitries; and contemporaneous with the detecting, receiving the information signal from the weight force sensing device.

5. The system of claim 4, wherein the plurality of pairs of emitter matched to sensor devices are arranged about the support ring such that the one or more beams are oriented in a detection region spanning across, and just below, the at least one port opening of the container.

6. The system of claim 4, wherein the plurality of pairs of emitter matched to sensor devices are optical emitters matched to optical sensor devices; and wherein the plurality of pairs of optical emitter matched to optical sensor devices are arranged about the support ring to blanket the at least one port opening with one or more optical beams from the plurality of pairs.

7. The system of claim 1, further comprising:

one or more RFID communication circuitries communicatively coupled with the processor, arranged proximate to the support ring and to a container that is supported by the support ring, wherein the container includes at least one RFID device that at least identifies container profile information of the particular container supported by the support ring; and wherein the processor, responsive to executing computer instructions, performs operations comprising:

detecting placement of the container in proximity to the support ring; and interrogating the at least one RFID device and wirelessly receiving and collecting container profile information of the particular container; and determining from the collected container profile information whether the particular container is identified by container profile information stored in a container profile data base of the surgical object and fluid monitoring system.

8. A surgical object and fluid monitoring system, comprising:

a support ring for securely supporting a container with at least one port opening of the container being disposed for receiving surgical objects placed into the container through the at least one port opening with the aid of gravity;

a hollow spine structure vertically oriented and comprising a channel with channel walls along the length of the hollow spine structure;

a rod movably disposed in the channel within the hollow spine structure, the rod moveable along the channel;

a weight force sensing device mechanically coupled to the rod, the support ring mechanically coupled to the rod, and the rod being in a moving arrangement that transfers weight force from the support ring to the weight force sensing device;

a flexure mechanically coupled with the rod and the hollow spine structure, the flexure adding very little if any downward force onto the rod and thereby onto the weight force sensing device while maintaining the rod vertically aligned in the channel with a gap separating the length of the rod from the channel walls, the gap allowing the rod to move vertically without friction from contact with the channel walls while the rod in the channel is protected from impact by the channel walls; and a processor communicatively coupled with the weight force sensing device, wherein the processor, responsive to executing computer instructions, performs operations comprising:

determining an incremental weight of the contents of the container from a surgical object placed into the container through the port opening, based at least on an information signal received from the weight force sensing device indicating a change in weight force sensed by the weight force sensing device contemporaneous with the placement of the surgical object into the container through the at least one port opening with the aid of gravity, wherein the gap in at least a portion of the length of the channel comprises a non-air gas separating the rod from the channel walls in the at least a portion of the channel, the gap comprising the non-air gas allowing the rod to move vertically without friction from contact with the channel walls in the at least a portion of the channel while the rod in the channel is protected from impact by the channel walls.

9. A surgical object and fluid monitoring system, comprising:

a support ring for securely supporting a container with at least one port opening of the container being disposed for receiving surgical objects placed into the container through the at least one port opening with the aid of gravity;

a hollow spine structure vertically oriented and comprising a channel with channel walls along the length of the hollow spine structure;

a rod movably disposed in the channel within the hollow spine structure, the rod moveable along the channel;

a weight force sensing device mechanically coupled to the rod, the support ring mechanically coupled to the rod, and the rod being in a moving arrangement that transfers weight force from the support ring to the weight force sensing device;

a flexure mechanically coupled with the rod and the hollow spine structure, the flexure adding very little if any downward force onto the rod and thereby onto the weight force sensing device while maintaining the rod vertically aligned in the channel with a gap separating the length of the rod from the channel walls, the gap allowing the rod to move vertically without friction from contact with the channel walls while the rod in the channel is protected from impact by the channel walls; and a processor communicatively coupled with the weight force sensing device, wherein the processor, responsive to executing computer instructions, performs operations comprising:

determining an incremental weight of the contents of the container from a surgical object placed into the container through the port opening, based at least on an information signal received from the weight force sensing device indicating a change in weight force sensed by the weight force sensing device contemporaneous with the placement of the surgical object into the container through the at least one port opening with the aid of gravity, wherein the gap in at least a portion of the length of the channel comprises a fluid separating the rod from the channel walls in the at least a portion of the channel, the gap comprising the fluid allowing the rod to move vertically without friction from contact with the channel walls in the at least a portion of the channel while the rod in the channel is protected from impact by the channel walls.

10. The system of claim 1,
wherein the flexure is mechanically coupled with a top of the rod and the hollow spine structure.

11. The system of claim 10, wherein:
the flexure provides tensioning spring force on the rod keeping the rod aligned in the channel and in mechanical contact with the weight force sensing device.

12. The system of claim 1, wherein:
the weight force sensing device comprises a load cell that is communicatively coupled with the processor.

13. The system of claim 1, further comprising:
a base structure that supports the hollow spine structure; and
wherein the weight force sensing device comprises a load cell that is located inside the base and is communicatively coupled with the processor.

14. The system of claim 1, wherein the support ring comprising one or more RFID communication circuitries communicatively coupled with the processor, and arranged proximate to the support ring and to at least one port opening of a container that is supported by the support ring; and wherein the processor, responsive to executing computer instructions, performs operations comprising:

detecting placement of a surgical object into the container through the at least one port opening by monitoring at least one RFID device of the surgical object being located in a detection region in the container and proximate to the one or more RFID communication circuitries;

identifying a type of the surgical object from information received by the one or more RFID communication circuitries from the at least one RFID device of the surgical object being located in the container and proximate to the one or more RFID communication circuitries;

counting the numbers and sorting the type of the surgical object placed into the container through the at least one port opening;

contemporaneous with the detecting, receiving an information signal from the weight force sensing device; and determining an incremental weight of the contents of the container from the surgical object placed into the container through the at least one port opening, based at least on the information signal received from the weight force sensing device indicating a change in weight force sensed by the weight force sensing device contemporaneous with the placement of the surgical object into the container through the one port opening with the aid of gravity.

15. The system of claim 14, wherein the processor, responsive to executing computer instructions, performs operations comprising:

determining that the received information signal from the weight force sensing device indicates a valid change in weight force sensed, within a tolerance limit, for an expected type of surgical object to place into the container through the at least one port opening with the aid of gravity.

16. The system of claim 14, wherein the at least one port opening comprises a plurality of port openings, and each of the plurality of port openings being sized and dimensioned for receiving a type of surgical object different from respective types of surgical objects received through each of the other port openings of the plurality of port openings, and wherein the support ring comprising a plurality of pairs of emitter matched to sensor devices arranged about the support ring to blanket each of the plurality of port openings with one or more beams from the plurality of pairs of emitter matched to sensor devices; and wherein the processor, responsive to executing computer instructions, performs operations comprising:
detecting placement of a surgical object into the container through one port opening of the plurality of port openings by at least one of:
monitoring at least a break in one of the one or more beams that blanket the one port opening, and
monitoring at least one RFID device of the surgical object being located in a detection region in the container and proximate to the one or more RFID communication circuitries; and
identifying a type of the surgical object by at least one of:
a) determining a type of the surgical object from information received by the one or more RFID communication circuitries from the at least one RFID device of the surgical object being located in the container and proximate to the one or more RFID communication circuitries;
b) determining a type of the surgical object from the detected one port opening of the plurality of port openings through which the surgical object was placed in the container; and
c) determining a type of the surgical object from at least one of a) and b) combined with the determined incremental weight of the contents of the container from the surgical object placed into the container through the one port opening, based at least on the information signal received from the weight force sensing device indicating a change in weight force sensed by the weight force sensing device contemporaneous with the placement of the surgical object into the container through the one port opening with the aid of gravity.

17. The system of claim 14, wherein the surgical object comprises a sponge; and wherein the processor, responsive to executing computer instructions, performs operations comprising:
determining a fluid weight of the sponge placed into the container through the at least one port opening by at least comparing the determined incremental weight of the contents of the container from the sponge placed into the container to an expected "dry" (non-fluid-filled) weight value for the identified type of the sponge.

18. The system of claim 17, wherein the processor, responsive to executing computer instructions, performs operations comprising:
accumulating a total amount of estimated fluid loss for a patient over a time period, based at least on the determined fluid weight of the sponge placed into the container being accumulated with a determined fluid weight of one or more sponges placed into the container through the at least one port opening with the aid of gravity.

19. A method, with a processor of an information processing system, for monitoring at least one surgical object placed into a container, the method comprising:
securely supporting a container having at least one port opening, the container supported with a rod vertically aligned and moveably disposed in a channel of a vertically oriented hollow spine structure with a gap separating the length of the rod from the channel walls, the gap allowing the rod to move vertically without friction from contact with the channel walls, the rod transferring a weight force from the supported container to a weight force sensing device mechanically coupled to the rod;
detecting, with one or more RFID communication circuitries communicatively coupled with a processor, placement of a surgical object including at least one RFID device into the container through one of the at least one port opening with the aid of gravity by the one or more RFID communication circuitries interrogating the at least one RFID device of the surgical object being placed into the container;
identifying a type of the surgical object from at least information received by the one or more RFID communication circuitries from the at least one RFID device of the surgical object being located in the container and proximate to the one or more RFID communication circuitries;
contemporaneous with the detecting, receiving an information signal that indicates an incremental weight force of the container; and
determining, with the processor, an incremental weight of the contents of the container from the surgical object placed into the container through the one port opening, based at least on the received information signal indicating a valid incremental change in weight of the contents of the container from the surgical object placed into the container through the one port opening with the aid of gravity.

20. The method of claim 19, wherein the detecting placement comprises:
detecting placement of the surgical object into the container through the one port opening of the plurality of port openings by at least monitoring a break in one of a plurality of beams that blanket the one port opening.

21. The method of claim 20, further comprising:
counting in real time, with the processor, the number of surgical objects placed into the container through the one port opening, based at least on the detecting placement.

22. The method of claim 19, further comprising:
determining a fluid weight of the surgical object placed into the container through the one port opening by at least comparing the determined incremental weight of the contents of the container from the surgical object placed into the container to an expected "dry" (non-fluid-filled) weight value for the identified type of the surgical object.

23. The method of claim 22, further comprising:
accumulating a total amount of estimated fluid loss for a patient over a time period, based at least on the determined fluid weight of the surgical object placed into the container being accumulated with a determined fluid weight of one or more surgical objects placed into the container through the at least one port opening with the aid of gravity.

* * * * *